United States Patent [19]

Krzyzewski

[11] Patent Number: 4,656,060

[45] Date of Patent: Apr. 7, 1987

[54] ARSENICAL CREOSOTE WOOD PRESERVATIVES

[76] Inventor: John Krzyzewski, 66 Ashburn Drive, Nepean, Ontario, K2E 6N3, Canada

[21] Appl. No.: 744,900

[22] Filed: Jun. 17, 1985

Related U.S. Application Data

[63] Continuation of Ser. No. 502,378, Jun. 8, 1983, abandoned.

[30] Foreign Application Priority Data

Sep. 28, 1982 [CA] Canada ................................ 412325

[51] Int. Cl.$^4$ ........................... C09D 5/14; B05D 3/02
[52] U.S. Cl. ................................ 427/397; 106/15.05; 106/16; 106/17; 106/18; 106/18.32; 106/18.36; 427/441; 428/541; 514/493; 514/494; 514/499; 514/504
[58] Field of Search .................. 106/15.05, 16, 17, 18, 106/18.32, 18.36; 427/397, 441; 428/541; 514/493, 494, 499, 504

[56] References Cited

U.S. PATENT DOCUMENTS 3,376,144  4/1968  Stutz ................................ 106/15.05

FOREIGN PATENT DOCUMENTS 1058353  7/1979  Canada .

*Primary Examiner*—Lorenzo B. Hayes
*Attorney, Agent, or Firm*—Millen & White

[57] ABSTRACT

A novel stable, homogeneous aqueous solution for application to wood surfaces is provided herein. The aqueous solution consists essentially of creosote, a conventional inorganic wood preservative component, ammonia and an oil. The oil and the creosote are present in specified proportions in the aqueous solution. When the solution is applied to wood, and the wood dried, a creosote-treated wood surface which may be painted is provided.

11 Claims, No Drawings

ARSENICAL CREOSOTE WOOD PRESERVATIVES

This application is a continuation of application Ser. No. 502,378, filed June 8, 1983, now abandoned.

BACKGROUND OF THE INVENTION (i) Field of the Invention

This invention relates to a system and method for the preservation of timber. In particular, it relates to compositions for preserving wooden poles, thereby prolonging the service life of wooden poles partially buried in the ground by treatment either before or after they are so partially buried and whether the poles are wet or dry.

(ii) Description of the Prior Art

The wood products with which the present invention is concerned are materials which are to have low aesthetic considerations, (e.g. foundation piles, poles, posts and fences, ties, marina structures, high-way and bridge construction, laminated systems for exterior use, and cooling towers. Such compositions and treatment procedures are designed to provide protection not only during the storage and the handling of the timber but also to provide protection during the final use of the timber. It also relates to the treated wood products so formed.

A piece of timber, due to the manner of its formation, possesses anisotropic structure which influence its properties and behaviour. To overcome and minimize these disadvantages a number of specific problems exist: the wood must be protected against degrading environmental factors (namely, moisture cycling, photodegradation and biological attack; the dimensional stability with respect to moisture cycling must be improved; photodegradation due to sunlight might be minimized; the resistance to biological attack (fungus) must be improved; and extractives which adversely affect the protective properties of coatings must be sealed within the wood.

Protective systems should impart not only protection against biological degradation, but also considerable weather resistance. The system should provide weather resistance with enhanced fire resistance.

Four classes of treatments are currently used in an attempt to meet these requirements. The first class is that of clear or pigmented penetrating systems which contain fungicides and water-repellent additives, e.g. polyethylene waxes and metal stearates in a non-aqueous solvent media. These treatments are deficient in that they must be repeated at regular intervals of about 1 to 2 years to provide a desired level of protection.

The second class is that of stains and sealers. These are normally synthetic resin solutions, usually pigmented and designed to penetrate the surface of the wood. These treatments as well are deficient, and should be repeated every one or two years in order to provide the required degree of protection.

The third class is that of paint systems. Such paint systems would normally consist of a primer and top coats. When well applied, these will provide protection from two to five years.

The fourth class is that of salt treatments. A number of salt treatments have been suggested, the most common of which are known as copper-chrome arsenate (CCA), acid-copper-chromate (ACC) and ammoniacal copper salts. Presently systems of this type are effective to provide relatively long term durability when applied by pressure impregnation techniques. While such systems are effective in preventing biological deterioration of wood and provide clean and paintable surfaces, they, however, suffer from several disadvantages. CCA preservatives have low stability under storage and processing conditions and penetration into wood is limited. ACC preservatives cannot penetrate refractory species but water repellency of wood treated by ACC is good. Ammoniacal copper salts provide extremely stable treating solutions and produce a treated wood product which is clean, in which the preservative penetrates deeply into the wood substance (particularly in the case of refractory species), but which provides only partial protection to the products against weathering. All systems provide products which are more or less colored; thus the natural appearance of wood is changed or covered by the colored preservative and so is unsuitable for aesthetrially pleasing materials. Furthermore, none of these systems provides protection against glowing combustion. The CCA systems are believed to become fixed in the wood by oxidation-reduction reactions associated with the chromic acid in the compositions and it is these same reactions which are believed adversely to affect stability and processing characteristics. Moreover, while providing a high level of protection against fungal attact, they provide only partial protection against weathering.

In addition, two main preserving systems are also used, namely, (1) creosote, and (2) pentachlorophenol in pole oil. These preserving systems are effective in (1) preventing fungal and insect attack on the wood substance; and (2) in preventing weathering of the timber. Both of these requirements are important where long life is required in wood exposed to the weather. However, these treatments suffer from several disadvantages. The most important of these is low cleanliness. Oil in these systems exudes to the surface making the wood unpleasant (dangerous) to handle, impossible to paint, and provides a surface which readily accumulates dirt.

Preservative systems which provide clean systems available at the present time are the oil-free pentachlorophenol systmes using liquified gas or highly chlorinated aliphatic hydrocarbons as a solvent and vehicle for pentachlorophenol. Data indicates that products produced by these processes are inferior in weather resistance to wood products impregnated by oil-borne preservatives. Moreover, neither of the above-mentioned systems protects the wood against glowing combustion.

Thus, each of the preserving systems mentioned above has disadvantages and these can be summarised as follows: The major disadvantage of the use of creosote and pentachlorophenol oil treatment is their low cleanliness and their lack of paintability. The major disadvantage of the use of copper-chrome-arsenate system is limited stability of the treating solution under processing conditions. The major disadvantage of the use of ammonical copper compounds is the lack of weathering resistance of the treated wood product. The major disadvantages of the use of oil-borne pentachlorophenol treatments is the lack of weathering properties relative to the creosote and pentachlorophenol-oil systems.

In the past, timbers, e.g. mooring piles were impregnated first with the water-borne inorganic mixed salts. Then, they were seasoned by kiln-drying, air seasoning, or some other method. They were then retreated with creosote. This procedure may take from several months to over a year. In Germany, it has been reported that the creosote treatment preceeds and the salt impregnation follows immediately or soon after. However, this introduces a problem of sludge formation, and disposal of contaminants which introduces yet another problem.

The main drawback of such double impregnation procedure is that processing is expensive because of the labour intensive operations of moving timbers to and from storage locations in a seasoning yard, and the delay in processing limited by the rate of moisture lost during seasoning. Also the creosote and water-borne solutions must be stored separately to avoid sludging problems. In any case, a certain amount of sludge does form because the solutions are used in tandem during processing.

It is frequently necessary to preserve timber products (against fungal attack, and marine borers) with two immiscible preservatives, i.e. creosote and inorganic salts. The reason is that neither creosote nor the inorganic salts (e.g. copper arsenate) are adequate to protect the timber when used alone.

Contemporary systems for heavy duty preservation of timber (e.g. as utility poles, piles, posts, bridge beams, lumber, etc.) frequently employed pentachlorophenol (PCP) as a reliable heavy duty preservative. Application to leave a clean surface involves processes like CELLON (trademark) LPG impregnation or the methylene chloride solvent treatment to drive the PCP into the wood providing a reasonably clean surface requiring no seasoning. However material treated with PCP by these processes, suffers from certain disadvantages, e.g. loss of PCP from wood sublimination and low water repellency and weather resistance. Both disadvantages result in lowering of service life when compared with wood treated by the older conventional PCP-oil-borne systems. This also results in limitations to use of the treated wood in closed poorly ventilated areas e.g. basements. The PCP-oil-borne systems have the major disadvantages of wood discoloration, oily unpaintible surfaces, stickiness and dirt retention.

These disadvantages (using the so-called clean processes) can be partially solved by raising the amount of preservative incorporated into the wood thus retaining the concentration level above or close to the effective threshold value enven after loss of some preservative, resulting in an acceptable service life. Adequate water-repellency and PCP retention, and elimination of the health hazard due to vapours of PCP, can be realized by additional painting or top-coating of the wood surface. Such additional treatments (use of excess PCP and/or top-coating) considerably increase the cost of the treated wood and in some places are not economical.

Telephone communication poles, and wooden power transmission poles will decay in line service (particularly at the ground/air interface) unless protected with wood preservatives. Generally, for a long service life (about 50 years or more), the poles are pressure impregnated with wood preservatives. These preservatives often lose effectiveness over a period of about 25 to about 35 years, generally in the groundline region (i.e. the ground/air interface) where conditions for leaching microbial activity and slow movement of preservative to the surrounding soil deplete the preservatives to ineffective levels. It is much more economical to apply a remedial form of preservative treatment to replenish the toxicity required at the groundline region than to replace the old poles with new impregnated ones. Poles which are given such remedial treatment with presently available preservatives are expected to last from about 5 to 15 years longer than if they had been left untreated. Hence, the groundline treatment must be repeated at about 5 to about 15 year intervals.

The need for prolonging the service life of existing poles is most urgent. Because many users of such poles cannot meet the demand for new pole requirements, existing poles must consequently be so improved that they will not require early replacement. This, in turn, means that the need for an improved form of groundline preservative is therefore urgently required.

A number of preservative mastics, or paste-type chemical formulations for groundline treatment exist. Most of these formulations contain pentachlorophenol in a suitable solvent, and non-leach resistant additives e.g., sodium fluoride and borax. Such formulations are generally applied to the groundline areas of utility poles in the form of bandages. However, since pentachlorophenol has been in short supply for the past few years and since the shortage may continue in the future, an alternative preservative is desirable. On the other hand, the non-leach resistant chemicals, when used alone, have a short life, and have been found not to be economically favourable.

While pentachlorophenol is very leach resistant, the rate of penetration of these systems is very slow, often requiring more than about 5 years for the toxic pentachlorophenol system to penetrate to about 1½ inch depth, It is believed that the pentachlorophenol bandages lose some of their effectiveness after about 10 to about 15 years following treatments, and that retreatments may be necessary at a maximum of about 15 year intervals. On the other hand, while sodium fluoride penetrates rapidly, the levels of retention are very often too low to be effective.

Pentachlorophenol, the main component of the above-described groundline preservatives, is oil soluble and is carried in solvents, e.g. grease, thickened oil base, etc. Consequently, the system is not essentially compatible with wet wood, i.e. wood which has water which is considerably above the fibre saturation point. A very high percentage of poles are wet at the butt ends where effective treatment is required. It has also been found that the toxic components in many of the commercial formulations of groundline bandage preservatives do not penetrate the entire sapwood depth in poles. Consequently, it is believed that suitable groundline treatment of poles may extend their service life by about 2 to 5 years.

A soluble borate, namely, sodium tetraborate in water has been used in "pressure-diffusion" treatments in Australia. Such process consists of impregnating round material with a high concentration of the borate in an abbreviated schedule (in the retort) and then stacking the material to allow deeper penetration by diffusion. However, this technique suffers the disadvantage that an expensive pressure system is necessary.

For maximum protection of timber from biodegradation, or marine organisms, it has been suggested that wood be treated in two stages. First it should be treated with an arsenical preservative, and subsequently (after a seasoning period) with creosote, or other suitable oil-borne preservative. These water-soluble arsenical salts, and either creosote, or an oil soluble preservative are deposited (impregnated) in the wood to be protected. It is also common practice to preserve timbers for use in marine structures for coastal locations by a two step operation. Arsenic salts are impregnated first, and after a period of seasoning (usually several months outdoors), the creosote is impregnated. Deposits of both creosote and arsenic salts are specified at high retentions, i.e. creosote at about 20 pounds per cubic foot (pcf), and arsenic at about 1.0 pcf. This labour intensive movement of timber into the yard for double periods of seasoning is obviously disadvantageous.

The present limitation is the requirement for the seasoning which may be conducted either by stacking in a storage yard, and atmospheric evaporation of the moisture, or by artificial seasoning in the treating retort. The artificial seasoning process can be completed within about 18 to about 30 hours by steaming or boiling under vacuum procedure carried out in the treating retort.

In the treating of timber it is self evident that the greater the penetration of the treating agent into the wood, the better the preservation. It has generally been the practice to treat the timber in two stages—first with water borne salts and, following a seasoning period (usually several months), then with an oil-borne component, or creosote.

In the area of "oil-borne preservatives" a breakthrough was made when new preservative carriers were developed which dissolved lipophilic preservatives adequately. Commonly, two solvents are used in North America, methylene dichloride and so-called liquefied petroleum gases. They penetrate into wood well and are recoverable from wood after treatment. Methylene dichloride is used in Canada also for treatment of spruce which it penetrates satisfactorily.

In the field of water-borne preservatives there was a similar need: to find a suitable solvent for spruce with good penetration characteristics.

It has been found that ponding or continuous spraying for a few months increases preservative penetrability of spruce so that a full sapwood penetration can be obtained by a standard pressure process. White spruce poles may be penetrated deeply and uniformly with creosote throughout the 1½-inch sapwood by standard impregnation processes when conditioned by freshwater ponding. Ponding now is carried out by floating debarked logs in fresh water for about 12 weeks at a mean temperature of about 65° F.

When creosote, or petroleum oils are mixed with ammonium hydroxide solution and agitated for thorough blending, almost immediate separation takes place upon storage of the mixture.

Water soluble phases and oil phases when mixed together are not miscible, generally separate rapidly, and frequently tend to produce sludges (which could not be used in wood preservation).

Arsenical creosote (AC) is well known. R. Johnson in the publication in a paper entitled "THE INCORPORATION OF ARSENIC IN CREOSOTE, PART 3* STABILITY OF ARSENICAL CREOSOTE IN THE PRESENCE OF WATER IN WOOD that equal amounts of arsenic can be incorporated with dry creosote or with creosote saturated with water. Heating of $As_2O_3$ with creosote at about 90° C., for about 4 hr. produces an arsenical creosote (AC) with a maximum arsenic content of about 0.5 percent $As_2O_3$. Higher temperatures increase the incorporation of $As_2O_3$ to a maximum of about 0.75 percent at about 200° C. and about 0.94 percent at about 220° C., but prelonged refluxing reduces the arsenical contents. The arsenical creosote was a heterogeneous mixture, not well suited for uniform treatment of timber.

A paper in the Forest Products Journal, Vol. 20, No. 11, November 1970 by M. P. Levi et al entitled "Distribution and Effectiveness in Pinus Sp. of a Water Repellent Additive for Water-Borne Wood Preservatives" discusses the development of a water repellent additive for use with water-borne CCA preservatives to overcome the deficiency of prevention of weathering degradation.

Ammonical copper arsenite compositions are presently being used as preservatives. Zinc arsenite compositions are also presently being used as preservatives. Zinc arsenate, zinc arsenite, and zinc phosphate can all be applied from an acetic acid solution and, on drying, the salt is insoluble and fixed in the wood. However, in all of these cases, the weather resistance of the treated wood is not significantly improved.

U.S. Pat. No. 1,145,186 patented July 6, 1915 by Eberhard provided an anticorrosive paint which was based on the fact that certain compounds of chromium soluble in oil or fat respectively, possess very valuable qualities for prevention of rust. These compounds have the same degree of oxidation as chromic acid, or an ethereal solution of chromic acid as well as of perchromic acid and also chromium phosphate dissolved in oil or fat. If linseed oil or varnish is acted upon in a suitable manner by chromyl chloride, and if a violent reaction is prevented, a clear viscid greenish purple oil, or a varnish respectively is obtained which proves to be highly valuable as a rust preventing means. To prevent an excessive action of chromyl chloride upon oils, varnishes, and the like, toluene, nitro-benzene, chloroform, aniline or similar hydrocarbons as well as bisulphide of carbon may be used.

U.S. Pat. No. 1,456,509 issued to A. Mai on May 29, 1923, taught that arsenic acids, sulfides of arsenic, Schweinfurt or Paris green and other arsenical compounds or mixtures may be brought in to solution to a large extent by the action of halogen inorganic substances or compounds with easily detachable halogen atoms, as, bromine or tribromide of arsenic, or with organic halogenical compounds or aliphatic or aromatic bodies containing several substituted halogen atoms, as phthalyl chloride, tribromacetic acid, tetrachloronaphthalene or mixtures thereof, in most of the organic solvents, e.g., acetone, ether, alcohol, amylacetate, ethylacetate, benzine, benzol, tar-oils, petroleum, etc., or in mixtures of any of these substances. Solutions of this kind have been said to have the advantage that they completely penetrate the wood in one single process, that they are not washed out and that according to the solvent selected they unite in themselves insecticidal and fungicidal qualities. Moreover, they have been said to permit the solution of inorganic preservatives, for example, naphthalene, anthracene, phenols, nitro-compounds, alkaloid salts, resins and the like, with the sole exception of the free bases; they are also solvents of sulfur.

It has still further been proposed (see U.S. Pat. No. 1,942,977 issued Jan. 9, 1934 to E. E. M. Payne) to treat wood products with a solution of one or more ammonium phosphates and then with a solution containing acid phosphates of magnesium and zinc, in order to precipitate an insoluble phosphate within the cell structure of the material, thereby to improve the color of the materials and to render the treated material resistant to fire.

Copper and zinc-containing fungicides which have been proposed (see U.S. Pat. No. 2,414,661 issued Jan. 21, 1947 to A. A. Nikitin), where prepared by precipitation of a zinc salt and a copper salt from an aqueous solution with an alkali solution containing soya bean protein, or soaps of fatty acids.

Fungicides, which have been proposed for cellulosic materials, (see U.S. Pat. No. 2,423,619 issued July 8, 1947 to L. Roon) comprise copper soaps formed in situ from an aqueous solution of copper salts and aqueous ammonia by reaction with fatty acids.

It has also been proposed to provide water and fire-resistant coatings on wood, (see U.S. Pat. No. 2,530,453 issued Nov. 21, 1950 to H. R. Frisch) by the use of zinc orthophosphate or zinc orthoarsenate compositions applied as a concentrated solution in aqueous ammonia.

It has been proposed, (see U.S. Pat. No. 2,722,263 issued Nov. 27, 1956 to C. C. Yeager) to use a compound having a high fungicidal activity in wood, which compound is a metal resin ammonium phenoxide-complex metal carboxylic acid soap compound, prepared by reacting a resin ammonium phenoxide with a water-soluble salt of a metal capable of forming a complex with ammonia.

It has been further proposed, (see U.S. Pat. No. 2,768,910 issued Oct. 30, 1956 to J. Krzikalla and O. Lissner) to improve the hardness, compressive strength, hydroscopicity and liability to swelling of wood by impregnating the wood with an aqueous ammoniacal solution of polycarboxylic acid containing at least six carbon atoms.

U.S. Pat. No. 2,875,020 issued Feb. 24, 1959 to R. G. Ring provides a wood preservative method and package including a porous fibrous oil and water permeable sheet, e.g. a porous fibrous material for example, fibrics and felted mats of vegetable fibres or glass fibre; a layer on one side only of the sheet of an inert, oil base carrier of grease-like consistency containing at least 2% pentachlorophenol, and a synthetic reservoir oil and water impervious film completely enclosing the sheet and layer, e.g. a sleeve of polyethylene, polyvinyl compounds, etc. Such procedure is labour intensive and undesirable.

U.S. Pat. No. 2,939,704 issued June 7, 1960 to C. E. Wilkinson provides a composition including a suitable asphalt base, cut back with a volatile diluent, as well as an inorganic filler consisting essentially of fine asbestos fibres, fine mica, fine vermiculate or fine alkali metal tetraborate. This suffers the disadvantage of lack of compatibility of the organic component (the asphalt), i.e. the most effective preservative constituent, with wet wood.

It has also been proposed, (see U.S. Pat. No. 3,007,844 issued Nov. 7, 1961 to W. O. Schuly) to use a composition comprising a heavy metal ion, borate ions and chromate ions as an impregnating agent for the preservation of wood.

It has further been proposed, (see U.S. Pat. No. 3,105,773 issued Oct. 1, 1963 to S. Frank and D. C. Wehner) to preserve wood by imparting pesticidal and anti-thallophytic properties thereby by first impregnating the wood with a water-soluble heavy metal salt, and with an acrylic polymer solution.

U.S. Pat. No. 3,376,144 issued Apr. 2, 1968 to R. E. Strutz provides a wood preservative composition thickened with a combination of a microcrystalline wax, water soluble non-ionic surfactant, and water, combined with a mixture of an organic wood preservative liquid and an alkaline inorganic alkali metal salt. This composition suffers the disadvantage of a low level of retention.

U.S. Pat. No. 3,390,951 issued July 2, 1968 to J. H. Finger et al provides a method of strengthening, preserving and extending the life of wooden poles by applying a metal band to the pole surrounding the zone of weakness with a fibrous resin impregnated material, and connecting tension means to the pole above the upper band means and below the lower band means and extending therebetween. This procedure suffers the disadvantage of being too labour intensive and provides a separate heterogenous addition to the pole.

U.S. Pat. No. 3,409,388 issued Nov. 5, 1968 to R. F. Nelson provides a method for preserving wooden poles by applying a bandage which is an elongated tube of preservative impermeable water soluble material, to spaced areas of the pole and dissolving the protective film to permit direct contact between the preservative and the pole. This suffers the disadvantage of low level of retention and of not providing optimum times of contact of the wrapped preservative with the wood.

U.S. Pat. No. 3,764,377 patented Oct. 9, 1973 by W. E. Keys provided a wood treating composition containing a novel arsenic compound that is compatible with creosote, and includes the toxic qualities of arsenic compounds as well as those of creosote. The novel organic arsenic compound is formed by the reaction of arsenous oxide ($AS_2O_3$) with N,N,N',N'-tetrakis(2-hydroxypropyl)ethylene diamine, and has the general structure

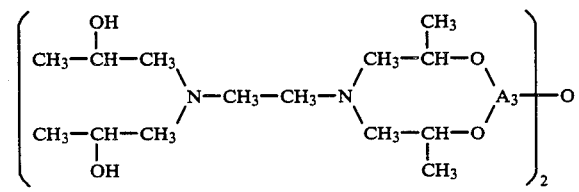

It has also been proposed, [see British Patent No. 1,220,281 published Jan. 27, 1971 in the name of Hickson's Timber Impregnation Co. (G.B.) Ltd.] to treat wood with an aqueous emulsion containing an aqueous solution of a wood preservative composition based on hexavalent chromium, a water-insoluble insecticide in a liquid hydrocarbon solvent, and a non-ionic surface active agent. The emulsion is used by impregnation of the wood by means of a pressure process, to provide protection against fungal attack and against a variety of insects.

Canadian Patent No. 515,610 provides a wood treating composition consisting essentially of a material selected from the group consisting of:
water miscible polyhydric alcohols having from 2 to 6 hydroxyl groups; solutions of boric acid in water miscible polyhydric alcohols having from 2 to 6 hydroxyl groups; solutions of an alkali metal borate in water miscible polyhydric alcohols having from 2 to 6 hydroxyl groups; boric acid esters of water miscible polyhydric alcohols having from 2 to 6 hydroxyl groups; and mixtures thereof contained in an impregnant selected from the group consisting of the tars and creosotes.

Canadian Patent No. 568,393 issued Jan. 6, 1959 to Bror O. Häger proposed to provide an agent for the preservation of wood including an aqueous ammoniacal solution of an amine-forming metal of the group consisting of copper, zinc, nickel, cobalt, cadmium and silver, and dissolved carbon dioxide of a content of at least two-thirds of the metal content. This composition is far too dilute to be used for groundline treatment. The same patentee, in Canadian Patent No. 960,959 issued Jan. 14, 1975, provided a composition consisting essentially of (1) a metal compound selected from the group consisting of the oxides, hydroxides, and carbonates of copper, zinc, nickel, cadmium and cobalt, and (2) a fatty acid having from 6 to 12 carbon atoms per molecule, dissolved in (3) an annomiacal water solution. Both these compositions suffer the disadvantage that they do not have optimum high water repellency, optimum low water uptake, optimum fast and high preservative penetration, and optimum resistance to arsenic leaching.

Canadian Patent No. 978,474 issued Nov. 25, 1975 naming Michael R. Clarke and Jaromir R. Rak as inventors, provides a dilute aqueous composition comprising a normally water-insoluble compound selected from zinc arsenate, zinc arsenite, copper arsenate, copper arsenite or mixtures thereof, a water repellent component, including a carbonate or bicarbonate and sufficient ammonia to dissolve the normally water-insoluble compound. This composition, while it is very useful, is too dilute to be used to preserve wooden poles at the groundline in the form of bandages. Also, the composition is not sufficiently compatible with wet poles.

Canadian Patent NO. 1,001,948 issued Dec. 21, 1976 naming Jaromir Rak as inventor provides a wood preservative composition imparting a clean surface and good service life to the wood substrate, comprising (a) an organic wood preservative agent, i.e. pentachlorophenol (as primary preservative); (b) a hydrophobic agent selected from fatty acids and their esters, fatty alcohols and various waxes, suitably having at least ten carbon atoms in the longest chain in the molecule; (c) an amorphous polymer; and (d) an organic solvent for (a), (b) and (c).

Canadian Patent No. 1,058,353 issued July 17, 1979 naming John Krzyzewski, as inventor provides a thickened ammonia-base wood treating composition for application as a covered layer to a wood surface, the composition comprising: (A) a preservative component which is one of (i) a normally water-insoluble salt selected from the group consisting of zinc arsenate, zinc arsenite, copper arsenate, copper arsenite and mixtures thereof; (ii) an ammonia-soluble salt selected from the group consisting of copper borate, zinc borate or mixtures thereof, and copper chromate, zinc chromate or mixtures thereof; or (iii) an ammonia dispersible organometallic compound selected from the group consisting of copper naphthenate, zinc naphthenate or mixtures thereof, copper-8-quinolinolate, zinc-8-quinolinelate or mixtures thereof, or tributyltin oxide; and (iv) sufficient aqueous ammonia, in a concentration of about 1 to about 28% by weight NH3 to solubilize the normally water-insoluble salt (i), or the ammonia-soluble salt (ii), or to disperse the organometallic compound (iii); and (B) a sufficient amount of thickener component selected from the group consisting of: (v) (a) a saturated fatty acid of 12 to 22 carbon atoms; (b) an unsaturated fatty acid of 12 to 22 carbon atoms; (c) a copper, zinc, sodium, potash, or amine salt of a saturated fatty acid of 12 to 22 carbon atoms; or (e) mixtures thereof; (vi) (a) asbestos screenings; (b) natural serpentine fibrous fragments; (c) mica flakes; (d) adipic acid plus asbestos screenings; (e) adipic acid plus natural serpentine fibrous fragments; or (f) adipic plus mica flakes; (vii) a mastic of (a) a petroleum fraction selected from oils and greases with one of (b) asbestos screenings; (c) natural serpentine fibrous fragments; (d) mica flakes; (e) adipic acid plus asbestos screenings; (f) adipic acid plus natural serpentine fibrous fragments; or (g) adipic acid plus mica flakes; and (viii) a metallic soap selected from an insoluble soap of naphthenic acid, octoic acid, 2-ethylhexoid acid, rosin acids or tall oil acids, with aluminum, calcium, cadmium, cobalt, copper, iron, lead, manganese, nickel, tin or zinc; to provide a thickened composition having a viscosity of at least 30 poises, and desirably to provide one composition of about 30 to about 120 poises, and another composition of about 250 to about 300 poises, the viscosity in poises being measured by a Brookfield Viscometer at 25° C.

SUMMARY OF THE INVENTION

(i) Aims of the Invention

While the use of the compositions outlined above has tended to provide a considerable level of protection against specific degrading agencies, none of them provides a suitable balance of properties for example, excellent stability, high weather resistance, paintability, good wood penetration and good water repellency. Additionally some of the compositions outlined provide in the one system not only the protective properties mentioned above, but also a measure of protection against fire and do not adversely affect the natural appearance of the treated wood.

Therefore, objects of this invention are to provide aqueous wood-treating solutions in which a suitable balanced improvement is provided in the following properties, namely: a good level of weather resistance; low mammalian toxicity; resistance to biological and fungal attack; resistance to water penetration; resistance to extractive staining; substantially no adverse effect on protection against glowing combustion, good adhesion properties between the wood and a coating, e.g. paint or glue, etc. later to be applied thereto; and no substantial adverse effect on lumber surfaces.

Another object of this invention is to provide a wood treating aqueous solution which may be used for treating wet poles.

Yet another object of this invention is to provide a wood treating aqueous solution having high levels of retention.

(ii) Statements of Invention

By this invention, an homogeneous creosote-containing aqueous ammonical composition is provided for application to a wood surface, the composition comprising (A) creosote in an amount of from about 21% to about 70% by weight; (B) a preservative component which is selected from the group consisting of (i) a normally water-insoluble salt selected from the group consisting of zinc arsenate, zinc arsenite, copper arsenate and copper arsenite and mixtures thereof; (ii) an ammonia-soluble salt selected from the group consisting of copper borate, zinc borate, or mixtures thereof, and copper chromate, zinc chromate, or mixtures thereof; (iii) an ammonia-dispersible organometallic compound selected from the group consisting of copper naphthenate, zinc naphthenate or mixtures thereof, copper-8-quinolinolate, zinc-8-quinolinolate or mixtures thereof, or tributyltin oxide, (iv) sufficient aqueous ammonia, in a concentration of about 1 to about 28% by weight NH3 to provide about 10% to about 60% by weight of water, thereby to solubilize the salt (i) or to solubilize the salt (ii) or to disperse the compound (iii), and a stable homogeneous, aqueous solution for application to wood surfaces, such stable, aqueous solution consisting essentially of: (A) creosote; (B) a preservative component which is selected from the group consisting of (i) a normally water-insoluble salt selected from the group consisting of zinc arsenate, zinc arsenite, copper arsenate and copper arsenite and mixtures thereof; (ii) an ammonia-soluble salt selected from the group consisting of copper borate, zinc borate, or mixtures thereof, and copper chromate, zinc chromate, or mixtures thereof; (iii) an ammonia-dispersible organometallic compound selected from the group consisting of copper naphthenate, zinc naphthenate or mixtures thereof, copper-8-quinolinolate, zinc-8-quinolinolate or mixtures thereof, or tributyltin oxide, and, with ether (i), (ii) or (iii), (iv) sufficient aqueous ammonia, in a concentration of about 1 to about 28% by weight $NH_3$ to solubilize the salt (ii) or to dissolve the salt (ii) or to disperse the compound (iii); and (C) a solvent for the compounds (A) and (B), the solvent being selected from the group consisting of fuel oil, pole treating oil, kerosene, tie-treating oil, waste crank oil, and a petroleum distillate; the solvent (C) being present in a sufficient amount, of about 13% to 80% by volume of the total aqueous solution, and the creosote (A) being present in an amount of from 7% to about 70% by volume of the total aqueous solution, thereby to provide the stable, homogeneous aqueous solution; wood, when such solution, is applied thereto, and when the wood is thereby providing a creosote-treated wood surface which may be painted.

By this invention a procedure is provided which comprises applying, to the surface of wood, the above-described stable, homogeneous aqueous solutions, thereby impregnating such wood, and then drying such surfaces with a resulting loss of ammonia, thereby providing a creosote-treated wood surface which may be painted. Accordingly, the invention also provides a method which includes the step of painting the creosote-treated wood.

(iii) Other Features of the Invention

By other features, the preservative component (B) may comprise one of the following: (A) (i) a normally water insoluble salt selected from the group consisting of zinc arsenate, zinc arsenite, copper arsenate, copper arsenite and mixtures thereof, and (ii) sufficient aqueous ammonia, in a concentration of about 1 to 28% by weight $NH_3$ to solubilize the salt (i); (b) (ii) an ammonia soluble salt selected from the group consisting of copper borate, zinc borate or mixtures thereof, and copper chromate, zinc chromate or mixtures thereof; and (iv) sufficient aqueous ammonia, in a concentration of about 1 to about 28% by weight $NH_3$ to solubilize the salt (ii); or (C) (iii) an ammonia dispersible organometallic compound selected from the group consisting of copper naphthenate, zinc naphthenate or mixtures thereof; copper-8-quinolinolate, zinc-8-quiloinolate or mixtures thereof; or tributyltin oxide; and (iv) sufficient aqueous ammonia, in a concentration of about 1 to about 28% by weight $NH_3$ to disperse the compound (iii).

By another feature, the aqueous solution includes an acrylic resin as a water repellency improving agent.

By a further feature, the aqueous solution includes zinc thiocyanate, copper-thiocyanate or mixtures thereof to increase toxicity.

By yet another feature, the aqueous solution includes about 0.1–about 4% by weight of at least one of copper arsenate, zinc arsenate, copper arsenite and zinc arsenite (as Zn or Cu or Zn+Cu metal) of the total aqueous solution; about 0.15 to about 10% by weight of the total aqueous solution of a carbonate or bicarbonate; and from about 15—about 26% ammonia.

By a further feature, the ratio of active preservative/ammonia/water in the preservative component (B) is about 20–40/15–25/65–35.

By another feature, component (B) comprises (a) a normally water-insoluble compound selected from the group consisting of zinc arsenate, zinc arsenite, copper arsenate, and copper arsenite and minerals thereof in an amount of about 0.1 to about 4% by weight (as Zn or Cu metal) of the total aqueous solution; (b) about 0.5 to about 10% by weight of the total aqueous solution of a water-repellent component comprising one of (i) a water-insoluble organic acidic compound having a solubility $\geq 0.2\%$ and in concentrated aqueous ammonia, the water-insoluble organic acidic compound being selected from the group consisting of a substantially water-insoluble saturated or unsaturated monocarboxylic acid having between 8 and 15 carbon atoms in the carboxylic acid; a substantially water-insoluble saturated or unsaturated monocarboxylic acid having between 8 and 15 carbon atoms in the carboxylic acid substituted with a hydrocarbon radical; a substantially water-insoluble saturated or unsaturated monocarboxylic acid having between 8 and 15 carbon atoms in the carboxylic acid substituted with a hydroxyl radical; a substantially water-insoluble saturated or unsaturated monocarboxylic acid having between 8 and 15 carbon atoms in the carboxylic acid substituted with a halogen; maleinized unsaturated fatty acids from animal or vegetable sources, and having an acid value of about 200 to about 500; maleinized unsaturated fatty acid esters from animal or vegetable sources and having an acid value of about 200 to about 500; maleinized unsaturated fatty acids, formed by the reaction of maleic acid with fatty polycarboxylic acids and having an acid value between about 200 and about 500; maleinized unsaturated fatty acids formed by the reaction of maleic alkyds with fatty polycarboxylic acids, and having an acid value between about 200 and about 500; maleinized unsaturated fatty acid resins formed by the reaction of maleic acid with fatty polycarboxylic acids, and having an acid value between about 200 and about 500; maleinized unsaturated fatty acid resins formed by the reaction of maleic alkyds with fatty polycarboxylic acids, and having an acid value between about 200 and about 500; aromatic carboxylic acids having an acid value between about 200 and about 500; acid esters of phosphoric acid with monohydric alcohols and having an acid value between about 200 and about 500; acid esters of phosphoric acid with fatty alcohols and having an acid value between about 200 and about 500; synthetic polycarboxylic acids having an acid value between about 200 and about 500, and mixtures thereof, in an amount of up to about 200% of the zinc or copper, or (ii) or (iii) a combination of the selected organic acidic compound and a carbonate or bicarbonate ion selected from the group consisting of zinc carbonate, zinc bicarbonate, copper carbonate and copper bicarbonate in an amount of up to about 150% of the zinc or copper; and (c) ammonia, in an amount of about 1 to about 28% by weight of the total aqueous solution; the ammonia being sufficient to solubilize the normally water-insoluble salt of zinc or copper and the normally water-insoluble water-repellent compound.

By a feature thereof, the organic acidic compound is selected from: monocarboxylic acids having between 8 and 15 carbon atoms; hydroxy substituted monocarboxylic acids having between 8 and 15 carbon atoms; alkoxy substituted monocarboxylic acids having between 8 and 15 carbon atoms; halogen substituted monocarboxylic acids having between 8 and 15 carbon atoms; saturated fatty acids having between 8 and 15 carbon atoms; unsaturated fatty acids having between 8 and 15 carbon atoms; polycarboxylic acids of acid value between about 200 and about 500; aromatic carboxylic acids of acid value between about 200 and about 500; acid esters of phosphoric acid with saturated monohydric alcohols having between 8 and 15 carbon atoms; and acid esters of phosphoric acid with unsaturated fatty alcohols having between 8 and 15 carbon atoms.

By another feature, the water repellent component has a solubility of about 0.5% in concentrated aqueous ammonia and comprise a substantially water-insoluble monocarboxylic acid having between 8 and 15 carbon atoms in the carboxylic acid and being selected from the group consisting of octanoic, nonanoic (pelargonic, capric (decanoic), lauric (dodecanoic) and myristic (tetradecanoic); and unsaturated fatty acids selected from the group consisting of $\Delta^{9,10}$-decylenic, and $\Delta^{9,10}$-dodecylenic.

By yet a further feature, the aqueous solution has a pH of about 9 or more and comprises an aqueous solution containing: at least one of (a) copper ammonium arsenate, (b) copper ammonium arsenite, (c) zinc ammonium arsenate, and (d) zinc ammonium arsenite, and (e) anions of the selected organic acidic component.

By another feature, the unsaturated fatty acids from animal or vegetable sources which are maleinized are derived from sardine oil, lard, coconut oil, sesame oil, soybean oil, tung oil or corn oil.

By a still further feature, the aqueous solution has a pH of about 9 or more and comprises an aqueous solution containing: (i) at least one of (a) copper ammonium arsenate, (b) copper ammonium arsenite, (c) zinc ammonium arsenate, (*d) zinc ammonium arsenite, and (ii) anions of both (e) an organic acidic component and (f) a carbonate or bicarbonate.

By yet a further feature, the aqueous solution contains: saturated monocarboxylic acids having between 8 to 15 carbon atoms, alkoxy substituted monocarboxylic acids having 8 to 15 carbon atoms and halogen substituted monocarboxylic acids having between 8 and 15 carbon atoms; unsaturated fatty acids having between 8 and 15 carbon atoms; mixed higher fatty acids, derived from animal or vegetable sources, maleinized with maleic acid or maleic anhydride and an inorganic carbonate.

By another feature the aqueous solution contains acid esters of phosphoric acids with monohydric alcohols or fatty alcohols, and zinc carbonate or copper carbonate.

By another feature, the aqueous solution contains copper arsenate and zinc arsenate.

By another feature, the aqueous solution may contain, as the preservative component one of the following (a) zinc arsenate, nonanoic acid, zinc carbonate, and an aqueous ammonia solution (about 7% by weight); (b) zinc arsenate, zinc carbonate, monododecyl phosphate, and an aqueous ammonia solution (about 7% by weight); (c) zinc arsenate, decanoic acid, zinc carbonate and an aqueous ammonia solution (about 10% by weight); (d) zinc arsenate, zinc oxide, ammonium carbonate, dibutyl phosphate, and an aqueous ammonia solution (about 10% by weight); (e) zinc metaborate, zinc carbonate, docanoic acid and an aqueous solution (about 5% by weight); (f) copper carbonate, copper arsenate, lauric acid, and an aqueous ammonia solution (about 5% by weight; (g) copper arsenate, decanoic acid, and aqueous ammonia solution (about 7% by weight); (h) copper carbonate, copper arsenite, dihexyl phosphate, and an aqueous ammonia solution (about 7% by weight); (i) copper carbonate, copper arsenate, decanoic acid and an aqueous ammonia solution (about 7% by weight) and (j) copper arsenate, copper carbonate, decanoic acid and an aqueous ammonia solution, (about 5% by weight).

By a further variant, the preservative (B) comprises (a) a soluble component adapted to form a normally water-insoluble compound of zinc or zinc and copper with arsenic acid or arsenious acid in an amount of about 0.1—about 4% by weight (as Zn or Zn+Cu metal) of the total aqueous solution, the weight ratio of zinc or zinc and copper (as oxides) to arsenic (as oxides) being about 1.5 or more; (b) about 0.15—about 10% by weight of the total aqueous solution of a water repellent component comprising at least one of carbonate and bicarbonate ions, in an amount of up to about 150% of the zinc or copper; and (c) ammonia, in an amount of about 1—about 28% by weight of the total aqueous solution.

By yet another feature the ratio of $CO_2/NH_3/Zn/As$ or $CO_2/NH_3/Zn+Cu/As$ is about 1.7–2.3/5.9–6.7/1-.9-2.9/0.9; and the ammonia is sufficient to solubilize the normally water-insoluble salts of zinc or zinc and copper and the normally water-insoluble water repellent compound.

By other features, the preservative component (B) may comprise one of the following: (a) zinc ammonium cations, arsenic or arsenious anions, and anions of a carbonate or a bicarbonate; (b) zinc ammonium cations and copper ammonium cations, arsenic or arsenious anions; and anions of a carbonate or a bicarbonate; (c) zinc ammonium cations, arsenic or arsenious anions, and (c) anions of a carbonate or a bicarbonate; or (d) zinc ammonium cations and copper ammonium cations, arsenic and arsenious anions, and anions of a carbonate and a bicarbonate.

By a further feature, the aqueous solution contains carbonates of zinc or zinc and copper.

By another feature, the aqueous solution contains zinc arsenate or zinc arsenite.

By a still further feature, the aqueous solution contains zinc arsenate and copper arsenate or zinc arsenite and copper arsenite.

By yet other features, component (B) in the aqueous solution may comprise (A) from about 1 to about 4 parts by volume of a composition comprising (a) copper ammonium cations, (b) arsenic or arsenious anions, and (c) anions of a carbonate or a bicarbonate; and (B) from about 1 to about 3 parts by volume of a composition comprising (a) zinc ammonium cations, (b) arsenic or arsenious anions and (c) anions of a carbonate or a bicarbonate, the Cu being present in from about 19 to about 75% by weight based on total metal or (C) about 3 parts by volume of a composition comprising (a) copper ammonium cations, (b) arsenic or arsenious anions, and (c) anions of a carbonate or a bicarbonate; and (D) 1 part by volume of a composition comprising (a) zinc ammonium cations, (b) arsenic or arsenious anions and (c)

anions of a carbonate or a bicarbonate, the Cu being present in about 60% by weight, based on total metal; or (E) 1 part by volume of a composition comprising (a) copper ammonium cations, (b) arsenic or arsenious anions, and (c) anions of a carbonate or a bicarbonate, and (F) 1 part by volume of a composition comprising (a) zinc ammonium cations, (b) arsenic or arsenious anions, and (c) anions of a carbonate or a bicarbonate, the Cu being present in 40% by weight of total metal; or (G) 1 part by volume of a composition comprising (a) copper ammonium cations, (b) arsenic or arsenious anions, and (c) anions of a carbonate or a bicarbonate, the Cu being present in about 19% by weight of a total metal; or (I)
- arsenic oxide ($As^{III}$): 1.2 parts by weight
- zinc oxide: 3.6 parts by weight
- $NH_4HCO_3$: 4.0 parts by weight aqueous ammonia solution (28% $NH_3$, 20 ml in 100 ml $H_2O$): 91.0 parts by weight (J)
- arsenic oxide ($As^v$): 1.4 parts by weight
- zinc oxide: 3.6 parts by weight
- $HN_4HCO_3$: 4.1 parts by weight
- aqueous ammonia solution (28% $NH_3$, 20 ml in 100 ml $H_2O$): 91.9 parts by weight (K)
- arsenic oxide ($As^v$): 1.4 parts by weight
- copper oxide: 1.8 parts by weight
- zinc oxide: 1.0 parts by weight
- annonium bicarbonate: 2.4 parts by weight
- aqueous ammonia solution (28% $NH_3$, 23.7 ml in 100 ml $H_2O$): 93.5 parts by weight (L)
- arsenic oxide ($As^v$): 1.4 parts by weight
- copper oxide: 1.2 parts by weight
- zinc oxide: 1.8 parts by weight
- aqueous ammonia solution (28% $NH_3$, 22.5 ml in 100 ml $H_2O$): 95.6 parts by weight or (M)
- arsenic oxide ($As^v$): 1.4 parts by weight
- copper oxide: 0.6 parts by weight
- zinc oxide: 2.7 parts by weight
- $NH_4HCO_3$: 3.5 parts by weight
- aqueous ammonia solution (28% $NH_3$, 21.2 ml in 100 ml $H_2O$): 91.8 parts by weight By a feature of the aqueous solution, the preservative component (B) may comprise: (i) a normally water-insoluble salt selected from the group consisting of zinc arsenate, zinc arsenite, copper arsenate, copper arsenite and mixtures thereof; and (iv) sufficient aqueous ammonia, in a concentration of about 1 to about 28% by weight $NH_3$ to solubilize the salt (i); or it may comprise: (A) (II) an ammonia-soluble salt selected from the group consisting of copper borate, zinc borate or mixtures thereof, and copper chromate, zinc chromate or mixtures thereof; and (iv) sufficient aqueous ammonia, in a concentration of about 1 to about 28% by weight $NH_3$ to solubilize the salt (ii); or it may comprise (A) (iii) an ammonia dispersible organometallic compound selected from the group consisting of copper naphthenate, zinc naphthenate or mixtures thereof, copper-8-quinolinolate, zinc-8-quinolinolate or mixtures thereof, or tributyltin oxide; and (iv) sufficient aqueous ammonia, in a concentration of about 1 to about 28% by weight $NH_3$ to disperse the compound (iii).

By a feature thereof, the preservative component (B) includes: an acrylic resin as a water repellency improving agent.

By a feature thereof, the preservative component (B) includes zinc thiocyanate, copper thiocyanate or mixtures thereof to increase toxicity.

By a feature thereof, the preservative component (B) includes about 0.1 to about 4% by weight copper arsenate, copper arsenite, zinc arsenate or zinc arsenite or mixtures thereof (as Zn and/or Cu metal) of the total aqueous solution; about 0.15 to about 10% by weight of the total aqueous solution of a carbonate or a bicarbonate; and from about 15—about 26% ammonia.

GENERALIZED DESCRIPTION OF THE INVENTION

Thus, completely unexpected results have been provided by mixing any of the wood preservative compositions used and described heretofore with ammonium hydroxide in the presence of a small amount of an oil-type solvent, e.g. a petroleum oil. This was found to be true for various oils, e.g. fuel oil (no. 2), pole treating oil, kerosene, tie treating oil, waste crank oil and the petroleum distillate known by the trade name VARSOL. Stable, uniform, single phase solutions were produced in a wide range of concentrations. Also, unexpected results are obtained when ammonium hydroxide was blended with a large volume of the oil, in the presence of even a small quantity of creosote. Once again, stable single phase solutions are obtained. Another unexpected result which was observed was that, in a particular blend in a range which was on the verge or instability, the addition of a small quantity of copper naphthenate, resulted in stability being restored.

The essence of this invention is the stabilization of creosote with a conventional wood preservative composition using ammonia and a specified oil-like homogenizing solvent, e.g. an oil. Thus, many types of wood preservative compositions may be used. One variant of wood preservative component comprises an aqueous solution containing (a) a normally water-insoluble compound of zinc or zinc and copper with arsenic acid or arsenious acid in an amount of about 0.1–about 4% by weight (as Zn or Zn+Cu metal) of the total aqueous solution, the weight ratio of zinc or zinc and copper (as oxides) to arsenic (as oxides) being about 1.5 or more; (b) about 0.15—about 10% by weight of the total aqueous solution of carbonate and/or bicarbonate ions in an amount of up to about 150% of the zinc or the zinc and copper; and (c) ammonia, in an amount of about 1—about 28% by weight of the total aqueous solution; and the ratio of $CO_2/NH_3/Zn/Ac$ or $CO_2/NH_3/Zn+Cu/As$ being about 1.7–2.3/5.9–6.7/1.9–2.9/0.9, the ammonia being sufficient to solubilize the normally water-insoluble salt of zinc or zinc and copper, and the carbonate and/or bicarbonate.

The constituents of the preservative component of this composition may range in concentration (expressed as percentage by weight of the total) as follows: 1. Zinc or zinc and copper arsenic compound, present as the arsenate or the arsenite with the weight ratio of zinc or zinc and copper (as oxides) to arsenic (as oxides) being about 1.5 or more, in an amount of about 0.1–4 (as Zn or Zn+Cu metal); 2. Carbonate and/or bicarbonate ions present in proportions ranging up to about 150% of the zinc and copper, in an amount of about 0.15—about 10; and 3. Ammonia, in an amount of about 1—about 28 and the banance, to 100%, water, and preferably with the ratio of $CO_2/NH_3/Zn/As$ or $CO_2/NH_3/Zn+Cu/As$ being about 1.7–2.3/5.9–6.7/1.9–2.9/0.9.

There are three classes of preservative components useful in this invention. One class comprises water-insoluble but ammonia-soluble zinc arsenate, zinc arsenite, copper arsenate or copper arsenite or mixtures thereof.

Another class includes water-soluble, ammonia-soluble salts, namely, copper metaborate or zinc metaborate or mixtures thereof or copper chromate or zinc chromate or mixtures thereof.

Another class includes water-soluble, ammonia-soluble salts, namely, copper metaborate or zinc metaborate or mixtures thereof or copper chromate or zinc chromate or mixtures thereof.

A third class includes water-insoluble, ammonia dispersible organometallics, e.g., copper naphthenate or zinc naphthenate or mixtures thereof, copper-8-quinolinolate or zinc-8-quinolinolate or mixtures thereof, or tributyltin oxide.

An especially preferred preservative component in the aqueous solution of this invention is based on copper and/or zinc ammonium complexes containing arsenic anions ($As^{III}$ or $As^{V}$) and other additives, all components being soluble in one common aqueous ammoniacal solution. In the above-noted composition, the preservative components, in the form of water-in-soluble salts of zinc or copper or mixture of these, are solubilized in admixture with certain specified water repellent compounds in the ammoniacal solution.

The preservative component in the aqueous solution of this invention comprises an aqueous solution containing: (a) a normally water-insoluble compound selected from the group consisting of zinc arsenate, zinc arsenite, copper arsenate, and copper arsenite and mixtures thereof in an amount of about 0.1 to about 4% by weight (as Zn or Cu metal) of the total aqueous solution; (b) about 0.15 to about 10% by weight of the total aqueous solution of a water repellent component comprising one of (i) a water insoluble organic acidic compound having a solubility of $\geq 0.2\%$ and in concentration aqueous ammonia, the water insoluble organic acid compound being selected from the group consisting of a substantially water-insoluble saturated or unsaturated monocarboxylic acid having between 8 and 15 carbon atoms in the carboxylic acid; a substantially water-insoluble saturated or unsaturated monocarboxylic acid having between 8 and 15 carbon atoms in the carboxylic acid substituted with a hydrocarbon radical; a substantially water-insoluble saturated or unsaturated monocarboxylic acid having between 8 and 15 carbon atoms in the carboxylic acid substituted with a hydroxyl radical; a substantially water-insoluble saturated or unsaturated monocarboxylic acid having between 8 and 15 carbon atoms in the carboxylic acid substituted with a halogen; maleinized unsaturated fatty acids from animal or vegetable sources, and having an acid value of 200 to 500; maleinized unsaturated fatty acid esters from animal or vegetable sources and having an acid value of about 200 to about 500; maleinized unsaturated fatty acids, formed by the reaction of maleic acid with fatty polycarboxylic acids and having an acid value between about 200 and about 500; maleinized unsaturated fatty acids formed by the reaction of maleic alkyds with fatty polycarboxylic acids, and having an acid value between about 200 and about 500; maleinized unsaturated fatty acid resins formed by the reaction of maleic acid with fatty polycarboxylic acids, and having an acid value between about 200 and about 500; maleinized unsaturated fatty acid resins formed by the reaction of maleic acid with fatty polycarboxylic acids, and having an acid value between about 200 and about 500; maleinized unsaturated fatty acid resins formed by the reaction of maleic alkyds with fatty polycarboxylic acids, and having an acid value between about 200 and about 500; aromatic carboxylic acids having an acid value between about 200 and about 500; acid esters of phosphoric acid with monohydric alcohols and having an acid value between about 200 and about 500; acid esters of phosphoric acid with fatty alcohols and having an acid value between about 200 and about 500; synthetic polycarboxylic acids having an acid value between about 200 and about 500, and mixtures thereof, in an amount of up to about 200% of the zinc or copper, or (ii) or (iii) a combination of the selected organic acidic compound and a carbonate or bicarbonate ion selected from the group consisting of zinc carbonate, zinc bicarbonate, copper carbonate and copper bicarbonate in an amount of up to about 150% of the zinc or copper; and (c) ammonia, in an amount of about 1 to about 28% by weight of the total aqueous solution; the ammonia being sufficient to solubilize the normally water-insoluble salt of zinc or copper and the normally water-insoluble water-repellent compound.

The constituents of the preservative component in the aqueous solution of this invention may range in concentration (expressed as percentage by weight of the total) as follows: 1. Zinc and/or copper arsenic compound, present as the arsenate or the arsenite, in an amount of about 0.1—about 4 (as Zn or Cu metal); 2. Water repellent compound being a water-insoluble organic acidic compound having a solubility $\geq 0.2$, the compound being present in proportions ranging between 0% and about 200% of the zinc or copper; or carbonate or bicarbonate ions present in proportions ranging between 0% and about 150% of the zinc or copper; or both the water-insoluble organic acid compound and the carbonate or bicarbonate in an amount of about 0.15—about 10; and 3. Ammonia, in an amount of about 1—about 28.

Whether copper and/or zinc is used, the organic acidic component may generally be defined as an acidic compound which is insoluble in water but which is capable of forming compounds with the metal ammonia complex which are soluble in aqueous ammoniacal solutions. The organic acidic component has a solubility of $\geq 0.5\%$, preferably about 3% in concentrated aqueous ammonia (about 28%). Such component may be a substantially water-insoluble monocarboxylic acid having between 8 and 15 carbon atoms in the carboxylic acid and being either unsubstituted or substituted with hydrocarbon radicals, hydroxyl radicals or halogens. Examples include capric (decanoic), lauric (dodecanoic), myristic (tetradecanoic); unsaturated fatty acids, for example $\Delta^{9,10}$-decylenic, $\Delta^{9,10}$-dodecylenic. The preferred materials are those saturated and unsaturated higher aliphatic acids containing from nine to fifteen carbon atoms. Other organic acidic compounds which may be used are maleinized unsaturated fatty acids or esters from animal or vegetable sources such as, for example, sardine and other fish oils, lard, coconut oil, sesame oil, soybean oil, tung oil, corn oil, and having an acid value of about 200—about 500; maleinized unsaturated fatty acids; oils and resins formed by the reaction of maleic acid or maleic alkyds with the fatty polycarboxylic acids having an acid value between about 200 and about 500; aromatic carboxylic acids and derivatives thereof having an acid value between about 200 and about 500; the acid esters of phosphoric acid with monohydric alcohols or fatty alcohols having an acid value between about 200 and about 500; condensation polymers in which the acid value is between about 200 and about 500; and any mixtures of the above. Other acids which may be used include synthetic polycarboxylic acids, for example, polyesters and alkyds having an acid value between about 200—about 500.

The above-identified organic acidic compounds may be used as the sole water repellent agent, or may be used in admixture with a carbonate ion, or a bicarbonate ion. The carbonate ion or bicarbonate ion can be provided either by selection of the zinc carbonate, zinc bicarbonate, copper carbonate or copper bicarbonate, or it can be formed by reaction of a suitable zinc or copper salt, e.g. the oxide with ammonium carbonate or ammonium bicarbonate in the ammonia solution. In addition, the carbonate or the bicarbonate may be used as the sole water repellent agent or may be used in admixture with the above-identified organic acidic compounds.

The organic acidic components used are those which are characterized in that they form compounds with copper and/or with zinc which are water-insoluble, but which are soluble to greater than about 0.2%, preferably greater than about 3%, in about 28% aqueous ammonia solution.

If the aqueous solution is one containing zinc ions, the wood material provided is one having high aesthetic considerations, while if the solution is one containing copper ions, the wood material provided is one having low aesthetic considerations. In either case, the essential presence or arsenic acids or arsenious acids or mixtures thereof in such composition results in a composition which protects the wood against biological degradation. When carboxylic acids and/or carbonic or bicarbonic acid ions are present in the composition, the composition imparts high water repellency and weather resistance to the wood. When carbonic or bicarbonic acid ions or mixtures thereof and also zinc ions are present in the composition, the composition imparts protection to the wood against glowing combustion.

The level of ammonia used in the preservative component of the aqueous solution described above is generally in excess of that required to form the copper or zinc salts or coordinating complexes; the pH of the aqueous compositions will generally be pH about 9 or higher. The non-volatile solids of the compositions may vary between about 1% and about 25% (in the case of zinc), or between about 1% and about 15% (in the case of copper, or mixtures of copper and zinc).

One embodiment of preservative component used in the compositions of this invention comprises an aqueous solution of zinc ammonium arsenate or arsenious complex with the water repellent additive in the form of a carbonate or carboxylic acids, as defined above, and is characterized by its ability to give rapid penetration into wood substance and which on drying leaves wood with its natural appearance and colour, resistant to biological deterioration, resistant to weathering and resistant to glowing combustion. The treating solution has excellent stability under processing conditions.

In another embodiment of preservative component used in the aqueous solution of this invention comprises an aqueous solution of a copper ammonium arsenic or arsenious complex with the water repellent additive in the form of carbonate of carboxylic acids, as defined above, and is characterized in that it renders the wood resistant to weathering and biological deterioration. The treating solution has excellent stability under processing conditions.

Another preservative component used in the aqueous solution of this invention is based on zinc or zinc and copper ammonium complexes containing arsenic anions ($As^{III}$ or $As^{V}$), with the weight ratio of zinc and copper (as oxides) to arsenic (as oxides) being about 1.5 or more, containing carbonate or bicarbonate ions, and preferably the weight ratio of $CO_2/NH_3/Zn/As$ or $CO_2/NH_3/Zn+Cu/As$ being about 1.7–2.3/5.9–6.7/1-.9–2.9/0.9, all components being soluble in one common aqueous ammoniacal solution. In the above-noted aqueous solution, the preservative compounds in the form of water-insoluble salts of zinc or a mixture of zinc and copper are solubilized in admixture with certain specified water repellent compounds in the ammoniacal solution.

Such preservative component used in the aqueous solution of this invention comprises an aqueous solution containing (a) a normally water-insoluble compound of zinc or zinc and copper with arsenic acid or arsenious acid in an amount of about 0.1—about 4% by weight (as Zn or Zn+Cu metal) of the total aqueous solution, the weight ratio of zinc or zinc and copper (as oxides) to arsenic (as oxides) being about 1.5 or more; (b) about 0.15—about 10% by weight of the total aqueous solution of carbonate and/or bicarbonate ions in an amount of up to about 150% of the zinc or the zinc and copper; and (c) ammonia, in an amount of about 1—about 28% by weight of the total aqueous solution; and the ratio of $CO_2/NH_3/Zn/As$ or $Co_2/NH_3Zn+Cu/As$ being about 1.7–2.3/5.9–6.7/1.9–2.9/0.9, the ammonia being sufficient to solubilize the normally water-insoluble salt of zinc or zinc and copper, and the carbonate and/or bicarbonate.

The constituents of the preservative component used in the aqueous solution of this invention may range in concentration (expressed as percentage by weight of the total) as follows: 1. Zinc or zinc and copper arsenic compound, present as the arsenate or the arsenite with the weight ratio of zinc or zinc and copper (as oxides) to arsenic (as oxides) being about 1.5 or more, in an amount of about 0.1—about 4 (as Zn or Zn+Cu metal); 2. Carbonate and/or bicarbonate ions present in proportions ranging up to about 150% of the zinc or zinc and copper, in an amount of about 0.15—about 10; and 3. Ammonia, in an amount of about 1—about 28; and the balance, to 100%, water, and preferably with the ratio of $CO_2/NH_3/Zn/As$ or $CO_2/NH_3Zn\_Cu/As$ being about 1.7–2.3/5.9–6.7/1.9–2.9/0.9.

One embodiment of such preservative component in the aqueous solution of this invention comprises an aqueous solution of a zinc ammonium arsenate or arsenious complex with the water repellent additive in the form of carbonate which is characterized by its ability to give rapid penetration into wood substance and which, on drying, leaves wood with its natural appearance and colour, resistant to biological deterioration, resistant to weathering and resistant to glowing combustion. The aqueous solution has excellent stability under processing conditions and has been found to have very low arsenic leachability.

Another preservative component in the composition of this invention comprises an aqueous solution of a copper ammonium arsenic or arsenious complex with the water repellent additive in the form of carbonate and/or bicarbonate, which is characterized in that it gives rapid penetration into the wood substance and which, on drying, renders the wood resistant to weathering and resistant to biological deterioration. The treating solution has excellent stability under processing conditions and has been found to have medium arsenic leachability.

It is also desirable to improve the water repellency of the treated wood by including, in the composition, an acrylic wax or acrylic resin.

As used herein, the term "acrylic resin" is intended to embrace any thermoplastic or thermosetting polymer or copolymer or acrylic acid, methacrylic acid, esters of these acids or acrylonitrile, and polymerized, in most instances from acrylonitrile and the methyl or ethyl esters of acrylic or methacrylic acid. This includes polyacrylates and polymethacrylates. Acrylic resins, having repeating acrylonitrile units ($-CH_2CH(CN)-$), and acrylic rubbers, e.g. nitrile rubber having the repeating units ($-CH_2CH=CHCH_2CH_2CH(CN)-$), are also included.

In order to provide added toxicity, it is desirable to add zinc and/or copper thiocyanate to provide improved compositions of this invention.

The ammoniacal based creosote aqueous solution of this invention have enhanced capability of penetrating wet wood during the extreme cold winter months. Remedial treatments of transmission poles, bridge piles, and wharf timbers could be applied in the late autumn when the water table is low and the preservative would be penetrated before the spring water levels are elevated.

The ammoniacal based creosote aqueous solution of this invention thus have wide utility. The arsenic-containing ammoniacal preservatives, as well as the arsenic-free formulations of aspects of this invention are particularly suitable (i.e. are substantially non-leachable) for the treatment of wood with high moisture content. The condition frequently occurs in utility poles set in low-lying areas and in bridge piles set in streams and in wharf piles.

One preservative component in the aqueous solution of this invention comprise an aqueous solution of a zinc ammonium arsenate or arsenious complex with the water repellent additive in the form of carbonate or carboxylic acids, as defined above, which is characterized by its ability to give rapid penetration into wood substance and which on drying leaves wood with its natural appearance and color, resistant to biological deterioration, resistant to weathering and resistant to glowing combustion. The aqueous solution has excellent stability under processing conditions.

One example of such component is
zinc meta arsenite: 1.5 parts by weight
zinc carbonate: 4.5 parts by weight
decanoic acid: 3 parts by weight
aqueous ammonia (5% ammonia in water): 91 parts by weight Another preservative component in the aqueous solution of this invention comprises an aqueous solution of a copper ammonium arsenic or arsenious complex with the water repellent additive in the form of carbonate or carboxylic acids, as defined above, which is characterized in that it gives rapid penetration into the wood substance and which, on drying renders the wood resistant to weathering and resistant to biological deterioration. The aqueous solution has excellent stability under processing conditions.

One example of such component is:
copper arsenate: 3 parts by weight
copper carbonate: 3 parts by weight
organic additive as e.g. decanoic acid: 2 parts by weight
aqueous ammonia (5% ammonia in water): 92 parts by weight The aqueous solutions described above may be applied to the wood by known application methods, for example, by brush, spray or dip treatments or by impregnation techniques.

Other preservative components in the aqueous solutions of this invention include the following:
(a)
zinc arsenate: 4 parts by weight
nonanoic acid: 2 parts by weight
zinc carbonate: 1 part by weight
aqueous ammonia solution (7%): 93 parts by weight
(b)
zinc arsenate: 4.5 parts by weight
zinc carbonate: 2.0 parts by weight
monododecyl phosphate: 0.2 parts by weight
aqueous ammonia solution (7%): 93.3 parts by weight
(c)
zinc arsenate: 1 part by weight
decanoic acid: 3 parts by weight
zinc carbonate: 3 parts by weight
aqueous ammonia solution (10%): 93 parts by weight
(d)
zinc arsenate: 1 part by weight
zinc oxide: 5 parts by weight
ammonium carbonate: 2 parts by weight
dibutyl phosphate: 0.2 parts by weight
aqueous ammonia solution (10%): 91.8 parts by weight
(e)
copper carbonate: 1 part by weight
copper arsenate: 1 part by weight
lauric acid: 0.5 parts by weight
aqueous ammonia solution (5): 98.5 parts by weight
(f)
copper arsenate: 3 parts by weight
decanoic acid: 3 parts by weight
aqueous ammonia solution (7%): 94 parts by weight
(g)
copper carbonate: 1 part by weight
copper arsenite: 1 part by weight:
nonanoic acid: 2 parts by weight
aqueous ammonia solution (7%): 96 parts by weight
(h)
copper carbonate: 1 part by weight
copper arsenite: 2 parts by weight
decanoic acid: 3 parts by weight
aqueous ammonia solution (7%): 94 parts by weight
(i)
arsenic oxide (III): 1.22 parts by weight
zinc oxide: 3.57 parts by weight
$NH_4HCO_3$: 4.12 parts by weight
aqueous ammonia (28% $NH_3$, 20 ml in 100 ml water): 91 parts by weight
(j)
arsenic oxide (V): 1.42 parts by weight
zinc oxide: 3.57 parts by weight
$NH_4HCO_3$: 4.12 parts by weight
aqueous ammonia (28% $NH_3$, 20 ml in 100 ml water): 90 parts by weight
(k)
arsenic oxide: 1.42 parts by weight
copper oxide: 2.43 parts by weight NH$_4$HCO$_3$: 1.80 parts by weight
aqueous ammonia (28% NH$_3$, 25 ml in 10 ml water): 94 parts by weight
(1) arsenic oxide: 1.4 parts by weight
copper oxide: 2.4 parts by weight
NH$_4$HCO$_3$: 1.8 parts by weight
aqueous ammonia (28% NH$_3$, 25 ml in 100 ml water): 94.4 parts by weight
(m)
arsenic oxide (III): 1.2 parts by weight
zinc oxide: 3.6 parts by weight
NH$_4$HCO$_3$: 4.2 parts by weight
aqueous ammonia (28% NH$_3$, 20 ml in 100 ml water): 91 parts by weight
(n)
arsenic oxide (V): 1.4 parts by weight
zinc oxide: 3.5 parts by weight
NH$_4$HCO$_3$: 4.1 parts by weight
aqueous ammonia (28% NH$_3$, 20 ml in 100 ml water): 90 parts by weight
(o) ZMA: zinc meta arsenite, commercial preservative

|  | ZMA (As$^{III}$) |
| --- | --- |
| Arsenic (III) oxide (g) | 1.22 |
| ZnO (g) | 0.50 |
| NH$_4$HCO$_3$ (g) | 0.58 |
| NH$_4$OH (28% NH$_3$; ml) | 20 |
| H$_2$O to volume (ml) | 100 |
| oxide concentration (%; w/v) | 1.72 |
| specific gravity (g/cm$^3$) | 0.996 |
| ratio $\frac{\text{metal oxide}}{\text{arsenic oxide}}$ in formulation | 0.41 |

(p) ACA: ammoniacal copper arsenite, commercial preservative (according to the AWPA Standard)

|  | ACA (As$^{III}$) |
| --- | --- |
| Arsenic (III) oxide (g) | 1.22 |
| CuO (g) | 1.41 |
| NH$_4$OH (28% NH$_3$; ml) | 25 |
| H$_2$O to volume (ml) | 100 |
| oxide concentration (%/ w/v) | 2.63 |
| specific gravity (g/cm$^3$) | 0.999 |
| ratio $\frac{\text{metal oxide}}{\text{arsenic oxide}}$ in formulation | 1.16 |

(q) CuAs: copper-arsenic component mixture derived from Cu-As content in CCA-C formulation (AWPA Standard)

|  | CuAs (As$^V$) |
| --- | --- |
| Arsenic (V) oxide (g) | 1.15 |
| CuO (g) | 0.62 |
| NH$_4$OH (28% NH$_3$; ml) | 25 |
| H$_2$O to volume (ml) | 100 |
| oxide concentration (%/ w/v) | 1.77 |
| specific gravity (g/cm$^3$) | 0.994 |
| ratio $\frac{\text{metal oxide}}{\text{arsenic oxide}}$ in formulation | 0.54 |

(r) St$_{CCA-C}$: basic copper arsenate with As content derived from CCA-C formulation

|  | St$_{CCA-C}$ (As$^V$) |
| --- | --- |
| Arsenic (V) oxide (g) | 1.15 |
| CuO (g) | 1.15 |
| NH$_4$OH (28% NH$_3$; ml) | 25 |
| H$_2$O to volume (ml) | 100 |
| oxide concentration (%; w/v) | 2.30 |
| specific gravity (g/cm$^3$) | 0.997 |
| ratio $\frac{\text{metal oxide}}{\text{arsenic oxide}}$ in formulation | 1.00 |

(t) St$_{CAA}$: basic copper arsenate with As content derived from CAA formulation

|  | St$_{CAA}$ (As$^V$) |
| --- | --- |
| Arsenic (V) oxide (g) | 1.42 |
| CuO (g) | 1.42 |
| NH$_4$OH (28% NH$_3$; ml) | 25 |
| H$_2$O to volume (ml) | 100 |
| oxide concentration (%; w/v) | 2.84 |
| specific gravity (g/cm$^3$) | 0.998 |
| ratio $\frac{\text{metal oxide}}{\text{arsenic oxide}}$ in formulation | 1.00 |

(t) CAA: copper-ammonia-additive system containing As$^V$, basically copper arsenate with an excess of copper oxide

|  | CAA (As$^V$) |
| --- | --- |
| Arsenic (V) oxide (g) | 1.42 |
| CuO (g) | 2.43 |
| NH$_4$NCO$_3$ (g) | 1.80 |
| NH$_4$OH (28% NH$_3$; ml) | 25 |
| H$_2$O to volume (ml) | 100 |
| oxide concentration (%; w/v) | 3.85 |
| specific gravity (g/cm$^3$) | 1.030 |
| ratio $\frac{\text{metal oxide}}{\text{arsenic oxide}}$ in formulation | 1.71 |

(u) ZAA (As$^{III,V}$): zinc-ammonia-additive system containing As$^{III}$ or As$^V$, basically zinc arsenate with an excess of zinc oxide, but, generally speaking, new formulation

|  | ZAA (As$^{III}$) | ZAA (As$^V$) |
| --- | --- | --- |
| Arsenic oxide (g) | 1.22 | 1.42 |
| ZnO (g) | 3.57 | 3.57 |
| NH$_4$HCO$_3$ (g) | 4.12 | 4.12 |
| NH$_4$OH (28% NH$_3$; ml) | 20 | 20 |
| H$_2$O to volume (ml) | 100 | 100 |
| oxide concentration | 4.79 | 4.99 |

|  | ZAA (As$^{III}$) | ZAA (As$^V$) |
| --- | --- | --- |
| (%; w/v) specific gravity (g/cm$^3$) | 1.040 | 1.049 |
| ratio $\frac{\text{metal oxide}}{\text{arsenic oxide}}$ in formulation | 2.92 | 2.51 |

(v) CZAA (3:1, 1:1, 1:3): mixture of CAA and ZAA in given ratios,

|  | CZAA (3:1) (As$^V$) | CZAA (1:1) (As$^V$) | CZAA (1:3) (As$^V$) |
| --- | --- | --- | --- |
| Arsenic (V) oxide (g) | 1.42 | 1.42 | 1.42 |
| CuO (g) | 1.82 | 1.21 | 0.61 |
| ZnO (g) | 0.89 | 1.79 | 2.68 |
| NH$_4$HCO$_3$ (g) | 2.38 | 2.96 | 3.54 |
| NH$_4$CH (28% NH$_3$; ml) | 23.7 | 22.5 | 21.2 |
| H$_2$O to volume (ml) | 100 | 100 | 100 |
| oxide concentration (%; w/v) | 4.13 | 4.42 | 4.71 |
| specific gravity (g/cm$^3$) | 1.034 | 1.039 | 1.043 |
| ratio $\frac{\text{metal oxide}}{\text{arsenic oxide}}$ in formulation | 1.91 | 2.11 | 2.32 |

(w) CCA-C (oxide based)
  16.04 g CrO$_3$
  6.24 g CuO
  11.48 g As$_2$O$_5$ filled up to 1000 ml with H$_2$O;
  3.4 percent salts on oxide basis;
  pH = 1.34
(x) CAA
  35 g CuCo$_3$.Cu(OH)$_2$
  18 g NH$_4$HCO$_3$
  250 ml NH$_4$OH (26% NH$_3$)
  20 g H$_3$A$_5$O$_4$ (71% As$_2$O$_5$)
  filled up to 1000 ml with H$_2$O;
  3.9 percent salts on oxide basis
(y) ZAA
  35.7 g ZnO '41.2 g Nh$_4$HCO$_3$
  200 ml H$_3$A$_5$O$_4$ (71% As$_2$O$_3$)
  diluted 1+4 by H$_2$O;
  5.0 percent salts on oxide basis

| (z) Copper Arsenate | By Weight | By Parts |
| --- | --- | --- |
| Copper (as basic copper carbonate) | 700 g | 3.5 |
| Arsenic (as H$_c$AsO$_4$ - 71%) | 400 g | 2.0 |
| Ammonia bicarbonate (NH$_4$HCO$_3$) | 360 g | 1.8 |
| Water of solution | 200 g | 1.0 |

This solution is dissolved in 26 percent ammonia water to a volume of 2100 ml (10.5 parts). The yield is approximately 30 percent active copper arsenate solids in 23 percent ammonia solution.

| (AA) Zinc Arsenate | By Weight | By Parts |
| --- | --- | --- |
| Zinc (as zinc osides) | 123.5 g | 2.9 |
| Arsenic (as H$_3$AsO$_4$ - 71%) | 84.7 g | 2.0 |
| Ammonia bicarbonate (NH$_4$HCO$_3$) | 142.3 g | 3.4 |

This solution is dissolved in 627 g (14.8 parts) of 26 percent ammonia water, to yield approximately 24 percent active zinc arsenate solids in 16.7 percent ammonia solution.

Zinc and/or copper is an excellent vehicle for ammoniacal zinc and/or copper borate and will hold about 5 to about 6 times its weight of solution. Water insoluble borates have not been used heretofore as the prime ingredient in groundline bandage treatments because of the solubility problems. The preservatives are generally used in water-soluble form and therefore remain leachable. Copper and/or zinc borate in the ammoniacal solution according to aspects of this invention penetrate wood as well as the arsenate and/or arsenite system of the previously described embodiments of this invention. The copper and/or zinc borate system of this invention have very high leach resistance.

The preservative aqueous solutions of this invention were developed as a penetrating preservative to enable the penetration of impermeable sapwood e.g. that of White Spruce poles. White Spruce can be penetrated after the poles are "ponded" for period of about 12 weeks.

Another feature of this invention pertains to impregnation of timber and wood using conventional pressure treating plant equipment.

Creosote is miscible with salts, e.g. copper/chrome-/arsenate (CCA), dissolved in about 20 percent acetic acid using copper naphthenate co-solvent (6%), dissolved in No. 2 fuel oil.

A principal characteristic of the aqueous solutions of this invention is that white spruce wood can be penetrated almost as well as if the poles were "ponded". Consequently, this represents a very great saving since poles may be processed without ponding, which as an estimate would save an amount of from $15 to $25 per pole (for conditioning). This conditioning would not be required with a homogeneous creosote preservative of this invention.

In the formulations described hereinbelow, the ammonium hydroxide was used at the industrial reagent concentration, i.e. about 26% ammonia. This was added with the chemical salts dissolved, and the resultant ammonia concentration was that which resulted from blending the total components with the particular formulation.

Solutions in a wide range of oil-phase and water-phase components were stable, the following conditions preferably being selected:

(1) Creosote content in range of at least about 7 to about 10 percent (2) Ammonia (NH$_3$) content in the range of at least about 4.5 to about 6 percent.

The high creosote homogenized aqueous solutions of this invention could be used for treatment of timbers for heavy duty service, e.g. marine timbers, piles, etc. The copper carbonate can be replaced with copper arsenate, and it would be advantageous to use up to about 2 percent of copper naphthenate.

The aqueous solutions of the invention have great advantages, namely, that creosote becomes locked-in after treatment (i.e. it becomes non-bleeding), are highly water repellent, and can protect inorganic chemicals from leaching. Certain salts, e.g. copper carbonate, may be highly effective as wood preservatives provided they would be protected from leaching. As a constituent of the ammoniacal preservative/creosote/oil aqueous solution of this invention, copper carbonate would enhance the fungicidal toxicity of the preservative and would thus remove the risk of presence of arsenic salts.

Zinc salts would also be introduced without any problem, with the advantage being that zinc salts improve the water repellency further.

Homogenized creosote/oil/ammoniacal copper arsenate and zinc arsenate preservatives may be prepared by first preparing copper arsenate and zinc arsenate solutions.

In other features of this invention, the following may be used as cosolvents: (1) Ammonium hydroxide, (2) Fuel Oil, (3) Copper Naphthenate, and (4) Creosote.

DESCRIPTION OF PREFERRED EMBODIMENTS

The following are examples of compositions within the scope of this invention.

EXAMPLES I–XIV

Preservative solutions were prepared, containing a range of creosote proportions plus water-borne constituents. These water-borne constituents may be not only copper arsenates, but also other copper, and zinc compounds which have fungicidal properties.

|   | Component | Percent (by Volume) | |
|---|---|---|---|
| I | Creosote | 26.2 | |
|   | Ammonium hydroxide | 40.5 | (5% arsenic salts) |
|   | Arsenic Salts | 5% | (in NH$_4$OH) |
|   | Pole oil | 33.3 | |
|   |   | 100. | |
| II | Creosote | 33 | |
|   | Fuel oil | 33 | |
|   | Cu Naphthenate | 1 | |
|   | Ammonium Hydroxyl (20%) | 33 | |
|   |   | 99 | |
| III | Creosote | 33 | |
|   | Fuel oil | 33 | |
|   | Copper Carbonate | 1 | (13% in NH$_4$OH) |
|   | Ammonium Hydroxide (20%) | 33 | |
| IV | Creosote | 33 | |
|   | Copper Naphthenate | 0.33 | (8% concentrate) |
|   | Ammonium Hydroxide | 9.9 | |
|   | Water | 23.1 | |
|   | Pole oil | 33.7 | |
|   |   | 100 | |
| V | Creosote | 33 | |
|   | Ammonium Hydroxide | 33 | |
|   | H$_3$ASO$_2$ (70%) | 15 | |
|   | Fuel oils (No. 2) preservative fortifier copper Naphthenate, copper-8-quinolinolate, etc. (in Fuel oil) | 33 | |
|   | Total | 99 | |
| VI | Creosote | 55% | |
|   | Ammonium hydroxide | 12% | |
|   | Copper Carbonate | 5% | (of NH$_4$OH) |
|   | Fuel oil (1% Cu Naph) | 13% | |
|   | Water | 20% | |
|   |   | 100 | |
| VII | Creosote | 55.5 | |
|   | Pole oil | 22.2 | |
|   | Copper carbonate | 0.7 | |
|   | Ammonium hydroxide | 3.0 | |
|   | Water | 10% | |
| VIII | Creosote | 25 | |
|   | Pole treating oil | 25 | |
|   | Amm. Hydrox. (26%) | 12 | |
|   | Water | 38 | |
|   |   | 100 | |

|   | Component | Percent (by Volume) | |
|---|---|---|---|
| IX | Creosote | 17 | |
|   | Pole oil | 10 | |
|   | Copper Naphthenate (10% Cu) | 3 | |
|   | Ammonium Hydroxide (6%) | 70 | |
|   |   | 100 | |
| X | Creosote | 16 | to 70 |
|   | Salts | 1 | to 12 |
|   | Ammonium Hydroxide | 3 | to 10 (26% form) |
|   | Cu naphthanate as cosolvent | 5 | to 20 (containing 0.5 to 2% Cu) |
| IX | Waste oil | 80 | (1% Cu naththenate) |
|   | Creosote | 10 | |
|   | Ammonium Hydroxide | 10 | |
|   |   | 100 | |
| XII | Waste oil | 57 | |
|   | Creosote | 21 | |
|   | Ammonium Hydroxide | 21 | |
|   |   | 99 | |
| XIII | Creosote | 55 | |
|   | Arsenic salts (12%) | 25 | (dissolved in 26% Ammonium Hydroxide) |
|   | Fuel oil (contains 2% copper naphthenate) | 2 | |
|   |   | 100 | |

EXAMPLES XIV AND XV

The preservative of Example IX was tested for the treatment of railway tie sections. At a retention of 20 Pounds Per Cubic Foot (pcf), this would deposit the following:

Creosote: 3.4 pcf.
Arsenic salts: 0.2 pcf.
Copper naphthenate: 0.06 pcf. (as copper)

Compare this with presently accepted levels of treatment as follows:

Creosote: 8 pcf.
or Arsenic salts: 0.4 pcf.
or Copper naphthenate: 0.08 pcf. (in pole treating oil).

Marine timbers treated by the full-cell process, for high gross retention with the formulation of Example XIII would deposit the following, at a gross of 30 pcf:

Creosote: 16.5 pcf.
Arsenic salts: 0.90 pcf.
Cu (as naphthenate): 0.12 pcf.
(This is a rather high Cu content).

The standard practice 20 pcf.creosote is required, plus 1.0 pcf. of arsenic salts.

Tests

The homogenized creosote aqueous solutions of this invention were tested for stability as follows:

Solutions were prepared in 500 ml. flasks and left standing in the hot sun, for two weeks, and examined without agitating the flask.

(1) Such solution containing about 16% creosote remained homogenous.
(2) Such solution containing about 50% creosote had a dark coloured layer at the bottom of the container (a glass gallon bottle). This layer was completely dissolved by gentle stirring.

The aqueous solutions range in color from an almost black solution (like straight creosote) to a light walnut color depending on the creosote content.

The aqueous solutions of aspects of this invention were stable in solutions containing about 6 percent of inorganic salts. Usually a water-borne solution containing about 1 to about 3 percent solids in water is employed to treat poles, other timbers. Thirty pcf. gross equals from about 0.3 to 0.9 pcf. salts. Consequently, a 6 percent solution of mixed salts would qualify for a wide variety of treatments.

One aqueous solution which was formulated for the preservation of poles of railway ties was prepared as follows:

Creosote content: 16.1 percent
Arsenic salts and copper arsenate: 1.7 percent

The solution was heated (to about 135° F. for about 3 hrs) in a closed retort, and then stored for about 8 months in an open container, as a stability test. The test showed that the composition was very stable, the viscosity was not measured but appeared to be comparable to No.2 Fuel Oil.

A simple form of homogeniety test of solution was based on chromatographic separation of mixed solutions applied to filter paper. For non-homogeneous solutions, the aqueous phase spreads out with in about 30 seconds and the oil phase follows slowly. For homogeneous solutions no separation occurs, and solutions were tested for: about 1 hour, about 24 hours, and about 168 hours (under a bell jar). Solutions having a range of creosote content described above (about 16 to about 70%) remained homogeneous.

The aqueous solutions of this invention are lighter than creosote. The specific gravity, for example ranges from about 0.775 to about 0.995 for practical preservative solutions. Two solutions which were left standing for about 8 months remained stable, i.e. the aqueous phase showed no signs of separation.

For the homogenized or creosote/arsenic aqueous solutions, ammonium hydroxide is the main cosolvent, and solutions remained stable for indefinite periods. Homogenized preservatives prepared as long as about 5 years ago, and tested experimentally and secretly by being stored in a garage, summer and winter, still appear to be stable and homogeneous.

When the outer limits of the water-phase is on the verge of being unstable the addition of a small amount of copper naphthenate restores the stability fully, i.e. copper naphthenate, may be used as cosolvent. The stability of the acid system was also tested as an acid cosolvent.

Additional tests were carried out as follows:

(A) Water-Adsorption test

Water absorption (resistance to moisture) was tested on groups of 6 blocks each ¾ inch cube, red pine spawood. Blocks were treated by full-cell, in small lab. apparatus and then submerged in water at a rate of 130 ml/block for about 60 minutes. This is a very severe test—blocks have a high proportion of end grain, and red pine is particularly permeable. Controls—included in test were: Creosote at 10 pcf., and Pole Oil at 8 pcf. (Note: 10 pcf. creosote is considered a heavy treatment for general purpose timbers)

End-matched specimens (3×8×48) white spruce heartwood were treated by the pressure process with the following:

(1) 50 percent creosote in No. 2 Fuel Oil.

(2) Ammoniacal preservative/creosote/oil (16.1% plus 1.7% copper arsenate salts).

| | | RESULTS OF ABSORPTION | |
|---|---|---|---|
| No. | MOISTURE % | POUNDS PER CUBIC FOOD Creo/F.O. inventive composition | % IMPROVEMENT OF inventive composition |
| 1 | 10.5 | 15.6 | 18.5 | 18.6 |
| 2 | 10.5 | 15.3 | 23.7 | 54.9 |
| 3 | 10.0 | 11.7 | 13.1 | 12.0 |
| 4 | 10.5 | 10.1 | 11.9 | 17.8 |
| 5 | 11.9 | 21.3 | 23.7 | 11.3 |
| Average | | 14.8 | 18.2 | 22.9 |

The above specimens were squared and judged to be heartwood. They were incised and the penetration of the inventive composition penetrated beyond the incised regions. This is very unusual for squared material, in general the penetration is for the depth of the incisions, and even this considered quite good. A second consideration was that the moisture content of these timbers was too low, they were seasoned indoors for some period. The absorption and penetration would have been expected to be somewhat higher if the moisture content had been about 22 to about 28% moisture content, (based on dry wood content.)

(B) Homogenity

Solutions were dispensed onto a No. 40 Whatman Filter paper, and the chromatographic spread of solution was observed for several hours under bell jar. If the solutions spread at a rate which clearly indicated that the solution was spreading as a "whole", it was considered to be homogeneous. Some of the early tests which defined the range of component concentrations were noted to spread at different rates, e.g. the water phase moved at a different rate from the oil phase.

(C) Stability under treating conditions

A representative solution was used in impregnation test conducted at about 140 F. (the temperature recommended for ammoniacal solutions), and the solution was re-heated in the retort under pressure several times, then checked for stability.

The test results were as follows:

The water absorption test was carried out as follows on 0.75 inch cube red pine sapwood blocks. 6 blocks were soaked in 140 ml. of water per block, and weighted after 1 minute, 6 minutes, and 65 minutes for the test.

As observed, the untreated control absorbed the most water, while the wood treated with ammoniacal preservative/creosote/oil composition of an aspect of this invention absorbed less than wood treated with creosote alone or with pole treating oil alone.

As observed, the average penetration of ammoniacal copper arsenate in incised white spruce heartwood measured at quartile points was 13.2 mm. The mean minimum penetration was 5.2 mm. (5 points had less than, or equal to 4 mm.) This was computed from the following Depth measured at Minimum points; mm.

7
8
4

-continued

| Depth measured at Minimum points; mm. |
| --- |
| 6 |
| 9 |
| 7 |
| 3 |
| 8 |
| 2 |
| 2 |
| 5 |
| 3 |
| 4 |
| Av. 5.2 mm. |

The penetration followed the incising pattern, and the proportion of the cross-section penetrated was about 45.0%.

As observed, the average penetration of the ammoniacal preservative/creosote/oil in incised spruce heartwood measured at quartile points was 16.8 mm. The mean minimum penetration was 9.8 mm. (min. depth at one point marked with an X was 7 mm.

The proportion of the cross-section penetrated was 54.35%.

As observed, the drops in the block treated with ammoniacal preservative/creosote/oil were generally intact.

The improvement of the absorption of the aqueous solutions of this invention is clearly indicated.

Thus, formulations have been provided which could be used for brushing treatments of checks and cracks in poles.

Comparison of penetration in White Spruce heartwood square timber.

(1) Inventive Composition (5.3 pcf creosote plus 0.1 pcf arsenic salts) against
(2) Ammoniacal copper arsenate (CAA)

| Depth measured at ¼ points around the square section: | | | |
| --- | --- | --- | --- |
| Inventive Composition | Minimum points | ACA | Minimum points |
| 16 | 11 | 13 | 7 |
| 15 | 7 | 14 | 8 |
| 22 | 9 | 11 | 4 |
| 18 | 10 | 16 | 6 |
| 10 | 12 | 13 | 9 |
| 16 |  | 15 | 7 |
| 16 |  | 16 | 3 |
| 16 |  | 11 | 8 |
| 15 |  | 8 | 2 |
| 18 |  | 15 | 2 |
| 23 |  | 14 | 5 |
| 17 |  | 14 | 3 |
|  |  |  | 4 |
| 16.8 | 9.8 | 13.2 | 5.2 |

Proportion of Crosssection penetrated (1) Area of Inventive composition treated specimen:

80×148:11840 sq. mm.

Total area penetrated (by calculation): 5833 sq. mm. or 49.26% of section.

(2) Area of CAA treated section:

$$86 \times 160 - \frac{(23 \times 23)}{2} : 1350 \text{ sq. mm.}$$

Total area penetrated (by calculation): 3680 sq. mm. or 27.26% of section.

Water Absorbtion test

Additional water absorbtion tests (resistance to moisture) was conducted on groups of 6 blocks each ¾ inch cube, red pine sapwood. Blocks were treated by a full-cell in small lab treating equipment. Blocks were submerged in water for 60 minutes. This is a very severe test-Blocks have a high proportion of end grain, and red pine is particularly permeable.

Controls: Included in test were: Creosote at 10 pcf., and pole oil at 8 pcf.

Note: 10 pcf. creosote is condidered a heavy treatment for general purpose timbers, and 8 pcf. pole oil is the standard used in penta treatments.

The results have been described hereinabove. The homogeneous creosote-containing aqueous solutions of this invention of this invention (5.3 pcf. creosote/0.1 pcf. arsenic salts, showed 35% lower absorbtion than the 10 pcf. creosote, and 129% lower absorbtion than 7.3 pcf. pole treating oil.

TEST OF WATER CONTACT ANGLE

Normally when water drops are placed on the surface of the end of red pine sapwood blocks, they diffuse into the wood very rapidly. In treated blocks it may take about 1 to about 10 minutes. In the case of the homogeneous creosote-containing aqueous solution of the invention, the water drops remained intact for a test period of 60 minutes, and they were still globules. Beyond that time the drops evaporated to such a small size that the test is impractical.

ABSORBTION AND PENETRATION TESTS

End-matched specimens (3×8×48) of white spruce heartwood were treated by the pressure process, with the following (1) 50 percent creosote in No. 2 fuel oil and with (2) the homogeneous creosote containing aqueous solution of this invention (about 16.1% creosote plus about 1.7% arsenic salts, in solution).

Results of absorbtion:

| No. | M.C. % | POUNDS OF ABSORBTION (PCF) Creo/fuel oil | Inventive composition | % Absorbtion improvement in the Composition of aspects of this invention |
| --- | --- | --- | --- | --- |
| 1 | 10.5 | 15.6 | 18.5 | 18.6 |
| 2 | 10.5 | 15.3 | 23.7 | 54.9 |
| 3 | 10.0 | 11.7 | 13.1 | 12.0 |
| 4 | 10.5 | 10.1 | 11.9 | 17.8 |
| 5 | 11.9 | 21.3 | 23.7 | 11.3 |
| Average |  | 14.8 | 18.2 | 22.9 |

This lumber was heartwood and incised as required for preservative treatments in general. The aqueous solution of this invention penetrated beyond the incised region. This is very unusual for squared material, since generally the penetration is barely to the depth of the incisions.

These timbers were seasoned indoors and had much too low a moisture content for optimum penetration of ammoniacal preservatives, since they appear to show better penetration when the moisture content is above about 30 percent (oven dry basis).

Properties of treated wood

No exudation of preservative can be noted, regardless of temperature, and the amount of preservative injected. This is an answer to the constant question—clean creosote treatments. The preserved wood appears to be paintable. Poles could be treated at higher moisture contents than required for penta treatments, for example.

Still further tests were carried out with the aqueous solution of this invention as follows:

(1) Comparative penetration of the aqueous solution of this invention and Ammoniacal Copper Arsenate (CAA), impregnated in side matched squared timbers of white spruce.

(2) Comparison of water repellency by means of contact water-angle, as shown by drops of water placed on end-grain of ¾ inch cube treated wood blocks of red pine sapwood, at exposure times of 2, 10, and 60 minutes.

These tests conducted on conventional preservatives showed that CAA was the most effective preservative for penetrating white spruce heartwood. However, in the above tests of the aqueous solution of this invention, the aqueous solution of this invention penetrated the white spruce somewhat better than the CAA, indicated hereinabove, along with the outline of the penetration patterns of each.

The water-angle test blocks are laid out as follows:

| Background: | 9 pcf creosote | 5.1 pcf creosote/0.2 pcf Cu oil (inventive composition) |
|---|---|---|
| Foreground: | Untreated control | 7.1 pcf pole treating oil. |

The water-angle tests show the rapid absorbtion of both the untreated control and the 7.0 pcf pole treating oil (This is equivalent to a 5% penta treatment, which is more or less standard). The creosote can be varied in a wide range. The aqueous solutions were stable in a range from 6 percent to a high of 55.5 percent creosote.

The range of ingredients in the ammonia cosolvent system were:

| Creosote | 16 to 70 percent (by weight) |
|---|---|
| Salts | 1 to 15 |
| Ammonium hydroxide (26%) | 3 to 10 |
| Cu (naphthenate) in petroleum | 5 to 50 (0.5 to 2% Cu (naph). |

Ammonium hydroxide considered a cosolvent (if no inorganic salts are present):

| Creosote | 40 |
|---|---|
| Cu (naphthenate) | 30 (1% in pole oil) |
| Ammonium hydroxyl | 30 (26% conc). |
| | 100 |

Copper Naphthenate may be considered a cosolvent. The aqueous ammoniacal salts were completely soluble in creosote using Copper Naphthenate as cosolvent, all solutions were clear, single phase.

Thus, by this invention, a aqueous preservative solution has now been provided which has the following properties:

(1) Stable aqueous solution of creosote and water-borne salt solutions ranging in creosote concentrations from about 16 to about 70 percent and a water-borne phase of about 60 to about 10 or about 15 percent, the remainder of composition is cosolvent (which is also fungicidal), about 90 percent or more of the mixed solution is active fungicidal preservative.

(2) Significantly greater water repellency is provided than 10 pcf creosote or 8 pcf petroleum (as used for penta solutions).

(3) The ammoniacal preservative/creosote/oil aqueous solution tested at 5 pcf. creosote plus 0.2 pcf. arsenic salts, had the appearance of dark walmut stained wood. No preservative residue would be rubbed off.

(4) Can be used to impregnate marine timbers with 20 pcf. creosote plus 0.9 pcf. arsenic salts, in a single operation.

(5) When tested under high temperature, and in freezing tests, the aqueous solutions containing about 40 percent or more of creosote were stable (in the deep freeze test), while aqueous solutions which were lower in creosote content separated in freezing.

(6) Several 1-gallon lots were stored outdoors during winter months in Ottawa, Canada and also stored indoors (in a warm basement) aqueous solutions were homogeneous after experimental, secret tests for 5 years.

Treatments are clean and should be well suited to the treatment of poles with difficult-to-penetrate sapwood, e.g. white spruce, Douglas fir (mountain), etc. Treatments would be adaptable to treatment of railway ties to enable the reduction of creosote and partial use of mixed salts to reduce the cost of treatments.

SUMMARY

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What I claim is:

1. A stable, homogeneous, aqueous solution for application to wood surfaces, said stable, aqueous solution consisting essentially of:

(A) creosote;

(B) a preservative component which is selected from the group consisting of (i) a normally water-insoluble salt selected from the group consisting of zinc arsenate, zinc arsenite, copper arsenate and copper arsenite and mixtures thereof;

(ii) an ammonia-soluble salt selected from the group consisting of copper borate, zinc borate, and mixtures thereof, and copper chromate, zinc chromate, and mixtures thereof;

(iii) an ammonia-dispersible organometallic compound selected from the group consisting of copper naphthenate, zinc naphthenate and mixtures thereof, copper-8-quinolinolate, zinc-8-quinolinolate and mixtures thereof, and tributyltin oxide;

and, with either (i), (ii) or (iii)

(iv) sufficient aqueous ammonia, in a concentration of about 1 to about 28% by weight $NH_3$ to solubilize said salt (i) or to dissolve said salt (ii) or to disperse said compound (iii); and (C) solvent for said compounds (A) and (B), said solvent being selected from the group consisting of fuel oil, pole treating oil, kerosene, tie-treating oil, waste crank oil, and a petroleum distillate; said solvent (C) being present in a sufficient amount, of about 13% to 80% by volume of the total aqueous solution, and said creosote (A) being present in an amount of from 7% to about 70% by volume of the total aqueous solution, thereby to provide said stable, homogeneous aqueous solution;

said aqueous solution being capable of providing a creosote-treated wood surface which may be painted.

2. The stable homogeneous aqueous solution of claim 1, wherein said preservative component (B) comprises:
(A)
(i) a normally water-insoluble salt selected from the group consisting of zinc arsenate, zinc arsenite, copper arsenate, copper arsenite, and mixtures thereof; and
(ii) sufficient aqueous ammonia, in a concentration of 1 to 28% by weight $NH_3$ to solubilize said salt (i).

3. The stable homogeneous aqueous solution of claim 1, wherein said preservative component (B) comprises:
(B)
(ii) an ammonia-soluble salt selected from the group consisting of copper borate, zinc borate, and mixtures thereof, and copper chromate, zinc chromate and mixtures thereof; and
(iv) sufficient aqueous ammonia, in a concentration of about 1 to about 28% by weight $NH_3$ to solubilize said salt.

4. The stable homogeneous aqueous solution of claim 1, wherein said preservative component (B) comprises:
(B)
(iii) an ammonia-dispersible organometallic compound selected from the group consisting of copper naphthenate, zinc naphthenate and mixtures thereof, copper-8-quinolinolate, zinc-8-quinolinolate and mixtures thereof, and tributyltin oxide; and
(iv) sufficient aqueous ammonia, in a concentration of about 1 to about 28% by weight $NH_3$ to disperse said compound (iii).

5. The stable homogeneous aqueous solution of claim 1, wherein said preservative component (B) comprises:
(a) a normally water-insoluble compound selected from the group consisting of zinc arsenate, zinc arsenite, copper arsenate, and copper arsenite and mixtures thereof in an amount of about 0.1 to about 4% by weight (as Zn or Cu metal) of the total aqueous solution;
(b) about 0.15 to about 10% by weight of the total aqueous solution of a water-repellent component selected from the group consisting of:
(i) a water-insoluble organic acidic compound having a solubility about 0.2% in concentrated aqueous ammonia, said water-insoluble organic acidic compound being selected from the group consisting of a substantially water-insoluble saturated or unsaturated monocarboxylic acid having between 8 and 15 carbon atoms in the carboxylic acid; a substantially water-insoluble saturated or unsaturated monocarboxylic acid having between 8 and 15 carbon atoms in the carboxylic acid substituted with a hydrocarbon radical; a substantially water-insoluble saturated or unsaturated monocarboxylic acid having between 8 and 15 carbon atoms in the carboxylic acid substituted with a hydroxyl radical; a substantially water-insoluble saturated or unsaturated monocarboxylic acid having between 8 and 15 carbon atoms in the carboxylic acid substituted with a halogen; maleinized unsaturated fatty acids from animal or vegetable sources, and having an acid value of about 200 to about 500; maleinized unsaturated fatty esters from animal or vegetable sources and having an acid value of about 200 to about 500; maleinized unsaturated fatty acids, formed by the reaction of maleic acid with fatty polycarboxylic acids and having an acid value between 200 and about 500; maleinized unsaturated fatty acids formed by the reaction of maleic alkyds with fatty polycarboxylic acids, and having an acid value between about 200 and about 500; maleinized unsaturated fatty acid resins formed by the reaction of maleic acid with fatty polycarboxylic acids, and having an acid value between about 200 and about 500; maleinized unsaturated fatty acid resins formed by the reaction of maleic alkyds with fatty polycarboxylic acids, and having an acid value between about 200 and about 500; aromatic carboxylic acids having an acid value between 200 and about 500; acid esters of phosphoric acid with monohydric alcohols and having an acid value between about 200 and about 500; acid esters of phosphoric acid with fatty alcohols and having an acid value between about 200 and about 500; and synthetic polycarboxylic acids having an acid value between about 200% of the zinc or copper;
(ii) a carbonate or bicarbonate ion selected from the group consisting of zinc carbonate, zinc bicarbonate, copper carbonate, and copper bicarbonate, in an amount of up to about 150% of the zinc or copper; and
(iii) a combination of said selected organic acidic compound and a carbonate or bicarbonate ion selected from the group consisting of zinc carbonate, zinc bicarbonate, copper carbonate and copper bicarbonate in an amount of up to about 150% of the zinc or copper; and
(c) ammonia, in an amount of about 1 to about 28% by weight of the total aqueous solution; the ammonia being sufficient to solubilize said normally water-insoluble salt of zinc or copper and said normally water-insoluble water-repellent compound.

6. The stable homogeneous aqueous solution of claim 1, wherein said preservative component (B) is selected from the group consisting of:
(a)
zinc arsenate,
nonanoic acid
zinc carbonate, and an
aqueous ammonia solution (about 10% by weight);
(b)
zinc arsenate
zinc carbonate
monododecyl phosphate and an
aqueous ammonia solution (about 7% by weight);
(c)
zinc arsenate
decanoic acid,
zinc carbonate, and an
aqueous ammonia solution (about 10% by weight);
(d)
zinc arsenate
zinc oxide
ammonium carbonate
dibutyl phosphate, and an aqueous ammonia solution (about 10% by weight);
(e)
  zinc metaarsenite,
  zinc carbonate,
  decanoic acid, and an
  aqueous ammonia solution (about 5% by weight);
(f)
  copper carbonate,
  copper arsenate,
  lauric acid, and an
  aqueous ammonia solution (about 5% by weight);
(g)
  copper arsenate,
  decanoic acid, and an
  aqueous ammonia solution (about 7% by weight)
(h)
  copper carbonate
  copper arsenite,
  dihexyl phosphate, and an
  aqueous ammonia solution (about 7% by weight);
(i)
  copper carbonate,
  copper arsenate
  decanoic acid, and an
  aqueous ammonia solution (about 7% by weight); and
(j)
  copper arsenate,
  copper carbonate,
  decanoic acid, and an
  aqueous ammonia solution (about 5% by weight).

7. The stable homogeneous aqueous solution of claim 1, wherein said preservative component (B) is selected from the group consisting of:
(a) soluble component adapted to form a normally water-insoluble compound of zinc or zinc and copper with arsenic acid or arsenious acid in an amount of about 0.1—about 4% by weight (as Zn or Zn+Cu metal) of the total aqueous solution, the weight ratio of zinc or zinc and copper (as oxides) to arsenic (as oxides) being about 1.5 or more;
(b) about 0.15—about 10% by weight of the total aqueous solution of a water repellent component comprising at least one of carbonate and bicarbonate ions, in an amount of up to about 150% of the zinc or copper; and
(c) ammonia, in an amount of about 1—about 28% by weight of the total aqueous solution.

8. A method for protecting wood which comprises: applying to the surfaces thereof the stable homogeneous aqueous solution as claimed in claim 1, causing impregnation of said wood; and then drying such wood with the resulting loss of ammonia; thereby providing a creosote treated wood surface which may be painted.

9. The method of claim 8 including the step of painting the creosote-treated wood surface.

10. Creosote-treated wood which has been treated according to the method of claim 8.

11. Painted, creosote-treated wood which has been treated and painted according to the method of claim 9.

* * * * *